(12) United States Patent  
Beadle et al.

(10) Patent No.: US 8,962,654 B2
(45) Date of Patent: Feb. 24, 2015

(54) 3,4-DIHYDROISOQUINOLIN-2(1H)-YL COMPOUNDS

(71) Applicant: Eli Lilly and Company, Indianapolis, IN (US)

(72) Inventors: Christopher David Beadle, Buckinghamshire (GB); David Andrew Coates, Indianapolis, IN (US); Junliang Hao, Carmel, IN (US); Joseph Herman Krushinski, Jr., Brownsburg, IN (US); Matthew Robert Reinhard, Indianapolis, IN (US); John Mehnert Schaus, Indianapolis, IN (US); Craig Daniel Wolfangel, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/287,239

(22) Filed: May 27, 2014

(65) Prior Publication Data

US 2014/0357664 A1    Dec. 4, 2014

Related U.S. Application Data

(60) Provisional application No. 61/905,329, filed on Nov. 18, 2013, provisional application No. 61/828,740, filed on May 30, 2013.

(51) Int. Cl.
C07D 217/16    (2006.01)
A61K 31/47    (2006.01)

(52) U.S. Cl.
CPC .................. C07D 217/16 (2013.01)
USPC ......................... 514/307; 546/146

(58) Field of Classification Search
None
See application file for complete search history.

(56) References Cited

U.S. PATENT DOCUMENTS

| 5,236,934 A | 8/1993 | VanAtten |
| 5,246,943 A * | 9/1993 | Blankley et al. .............. 514/307 |
| 6,469,024 B2 | 10/2002 | Li et al. |
| 7,541,466 B2 | 6/2009 | Pregel et al. |
| 7,601,739 B2 | 10/2009 | Danso-Danquah et al. |
| 2006/0287359 A1 | 12/2006 | Danso-Danquah et al. |

FOREIGN PATENT DOCUMENTS

| EP | 330360 A1 | 2/1989 |
| WO | 9928314 A1 | 6/1999 |
| WO | 9942456 A2 | 8/1999 |
| WO | 0185695 A1 | 11/2001 |
| WO | 2013093842 A1 | 6/2013 |

OTHER PUBLICATIONS

Liao et al, Tetrahedron, vol. 65, Issues 29-30, Jul. 18, 2009, pp. 5709-5715.*
Soriano, Aroa et al., "A Hybrid Indoloquinolizidine/Peptide As Allosteric Modulator of Dopamine D1 Receptors", JPET Fast Forward. Published on Dec. 21, 2009 as DOI:10.1124/jpet.109.158824.
Giovanni, Andrew et al., "Design and synthesis of D1 agonist/D2 antagonist for treatment of schizophrenia", Bioorganic & Medicinal Chemistry Letters 23 (2013) 1498-1501.
VanAtten, Mary K. et al., "A Novel Series of Selective, Non-Peptide Inhibitors of Angiotensin II Binding to the AT2 Site", Journal of Medicinal Chemistry, (1993) vol. 36, No. 25.

* cited by examiner

*Primary Examiner* — Zinna Northington Davis
(74) *Attorney, Agent, or Firm* — Mark A. Winter

(57) ABSTRACT

The invention provides certain 3,4-dihydroisoquinolin-2 (1H)-yl compounds, particularly compounds of formula I, and pharmaceutical compositions thereof. The invention further provides methods of using a compound of formula I to treat cognitive impairment associated with Parkinson's disease or schizophrenia.

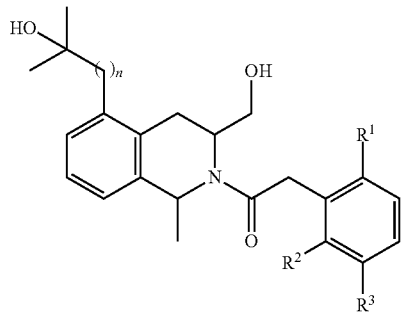

13 Claims, No Drawings

3,4-DIHYDROISOQUINOLIN-2(1H)-YL COMPOUNDS

CONTINUING DATA

This application claims benefit of 61/905,329 filed Nov. 18, 2013 and claims benefit of 61/828,740 filed May 30, 2013.

The invention provides certain 3,4-dihydroisoquinolin-2 (1H)-yl compounds, pharmaceutical compositions thereof, methods of using the same, and processes for preparing the same.

Parkinson's disease is a chronic, progressive, neurodegenerative disorder characterized by the loss of dopaminergic neurons in the brain. Parkinson's disease manifests in resting tremor along with other motor symptoms (e.g. akinesia and bradykinesia) and non-motor symptoms (e.g. cognitive impairment, sleep disorders, and depression). Current therapy for treatment of Parkinson's disease includes dopamine precursors such as levodopa, and dopamine agonists such as pramipexole. Such direct acting dopamine therapies are limited in effectiveness due in part to high dose associated cognition impairment, seizure risk (as shown in rodents for certain D1 agonists), and tolerance development. There remains a significant unmet need for safe and effective treatment of Parkinson's disease.

Allosteric modulators are agents that remotely alter the interactions of ligands with their receptors by modifying the ligand-binding environment. An example of this type of modulation is when the binding of a modulator to an allosteric (secondary) site produces a conformational change in the receptor protein that is transmitted to the ligand's orthosteric (primary) binding site. The quality of the allosteric effect is said to be positive if the modulator facilitates or potentiates an interaction or negative if it inhibits an interaction of the ligand with the orthosteric binding site.

Compounds of the present invention are positive allosteric modulators (PAMs) of the dopamine 1 receptor (D1). As such, compounds of the present invention are useful for the treatment of conditions in which D1 plays a role such as Parkinson's disease and schizophrenia, including relief of associated symptoms such as mild cognitive impairment in Parkinson's disease as well as cognitive impairment and negative symptoms in schizophrenia. Compounds of the present invention are also believed to be useful in treating symptoms of Alzheimer's disease such as cognitive impairment. Compounds of the present invention are also useful in improving motor symptoms in Parkinson's disease as a monotherapy. As well, compounds of present invention are believed useful in treating depression and attention deficit-hyperactivity disorder (ADHD).

The present invention provides certain new compounds that are PAMs of the D1 receptor and, as such, are useful in treatment of the disorders discussed above. The new compounds of the present invention may provide an alternative treatment for the such disorders. The present invention further provides a cocrystalline form of certain new compounds.

European Patent Application Publication No. EP 330360 discloses certain isoquinoline compounds as agonists of the opioid Kappa-receptor and useful as analgesics.

U.S. Pat. No. 5,236,934 discloses certain 1,2,3,4-tetrahydroisoquinoline compounds as inhibitors of the angiotensin II receptor and useful in treating CNS disorders including cognitive dysfunction.

U.S. Patent Application Publication No. US 2006/0287359 discloses certain tetrahydroisoquinoline compounds as estrogen receptor antagonists and useful in treating estrogen related diseases including breast cancer.

The present invention provides a compound of formula I

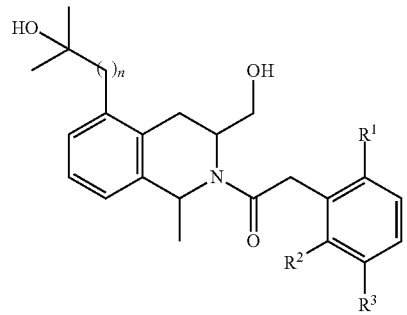

I wherein
n is 0, 1 or 2;
$R^1$ is halogen;
$R^2$ is halogen, H, CN, C1-C3 alkoxy or C1-C3 alkyl; and
$R^3$ is H, halogen, C1-C3 alkoxy or C1-C3 alkyl.

The present invention further provides a compound of formula Ia

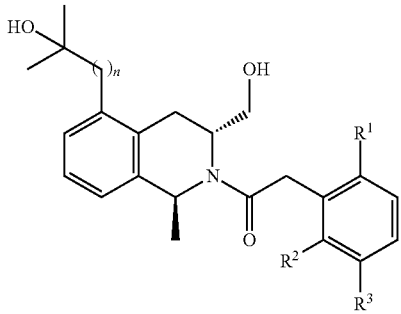

Ia wherein
n is 0, 1 or 2;
$R^1$ is halogen;
$R^2$ is halogen, H, CN, C1-C3 alkoxy or C1-C3 alkyl; and
$R^3$ is H, halogen, C1-C3 alkoxy or C1-C3 alkyl.

The present invention further provides a compound of formula I or Ia
wherein
n is 0, 1 or 2;
$R^1$ is halogen;
$R^2$ is halogen; and
$R^3$ is H or C1-C3 alkoxy.

The present invention further provides a compound of formula I or Ia
wherein
n is 0, 1 or 2;
$R^1$ is Cl, F or Br;
$R^2$ is Cl, $OCH_3$, H, F, CN or $CH_3$; and
$R^3$ is $OCH_3$, H, $CH_2CH_3$, Cl, $OCH(CH_3)_2$, $OCH_2CH_3$, F, $CH(CH_3)_2$ or $CH_3$.

The present invention further provides a compound of formula I or Ia
n is 0 or 2;
$R^1$ is Cl;
$R^2$ is Cl or F; and
$R^3$ is H or $OCH_3$.

The present invention further provides a compound of formula Ib

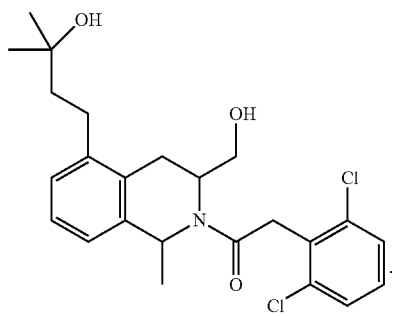

Ib

A particular compound of formula I is a compound of formula Ic.

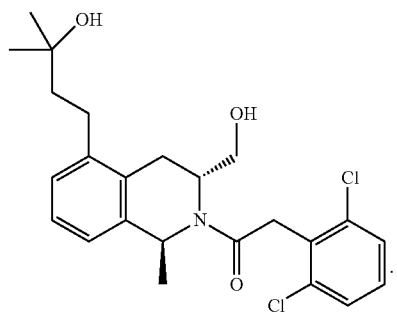

Ic

A particular compound of formula I is 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone.

The present invention further provides a composition comprising 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid.

The present invention further provides a composition comprising 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid in a ratio of about one to one.

The present invention further provides a cocrystalline form of a composition comprising 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid.

The present invention further provides a stable cocrystalline form of a composition comprising 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl] ethanone and 4-hydroxybenzoic acid.

The present invention further provides a cocrystalline form of a composition comprising 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid characterized by an X-ray powder diffraction pattern using CuKa radiation having a diffraction peak at diffraction angle 2-theta of 18.2° in combination with one or more of the peaks selected from the group consisting of 16.0°, 25.4°, and 7.0°; with a tolerance for the diffraction angles of 0.2 degrees.

A particular compound of formula I is 2-(2,6-dichlorophenyl)-1-((1S,3R)-3-(hydroxymethyl)-5-(2-hydroxypropan-2-yl)-1-methyl-3,4-dihydroisoquinolin-2(1H)-yl)ethan-1-one.

The present invention further provides a crystalline form of 2-(2,6-dichlorophenyl)-1-((1S,3R)-3-(hydroxymethyl)-5-(2-hydroxypropan-2-yl)-1-methyl-3,4-dihydroisoquinolin-2(1H)-yl)ethan-1-one characterized by an X-ray powder diffraction pattern using CuKα radiation having a diffraction peak at diffraction angle 2-theta of 14.27° in combination with one or more of the peaks selected from the group consisting of 15.71°, 18.01°, 18.68°, 22.43°, and 25.08°; with a tolerance for the diffraction angles of 0.2 degrees.

Further, the present invention provides a pharmaceutical composition comprising a compound of formula I, and a pharmaceutically acceptable carrier, diluent or excipient.

Further, the present invention provides a method of treating Parkinson's disease comprising administrating to a patient in need thereof an effective amount of a compound of formula I.

Further, the present invention provides a method of treating neurocognitive disorders associated with Parkinson's disease comprising administrating to a patient in need thereof an effective amount of a compound of formula I.

Further, the present invention provides a method of treating schizophrenia comprising administrating to a patient in need thereof an effective amount of a compound of formula I.

Further, the present invention provides a method of treating Alzheimer's disease comprising administrating to a patient in need thereof an effective amount of a compound of formula I.

Further, the present invention provides a compound of formula I for use in therapy.

Further, the present invention provides a compound of formula I for use as a medicament.

Further, the present invention provides a compound of formula I for use in the treatment of Parkinson's disease.

Further, the present invention provides a compound of formula I for use in the treatment of schizophrenia.

Further, the present invention provides a compound of formula I for use in the treatment of Alzheimer's disease.

Further, the present invention provides the use of a compound of formula I for the manufacture of a medicament for Parkinson's disease.

Further, the present invention provides a pharmaceutical composition comprising 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid, and a pharmaceutically acceptable carrier, diluent or excipient.

A compound of formula I may be used in combination with other drugs that are used in the treatment/prevention/suppression or amelioration of the diseases or conditions for which compounds of formula I are useful including Parkinson's disease and schizophrenia. Such other drug(s) may be administered, by a route and in an amount commonly used therefore, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I. Examples of other active ingredients effective in the treatment of Parkinson's disease that may be combined with a compound of formula I, either administered separately or in the same pharmaceutical composition include, but are not limited to:

(a) dopamine precursors such as levodopa; melevodopa, and etilevodopa; and (b) dopamine agonists including pramipexole, ropinirole, apomorphine, rotigotine, bromocriptine, cabergoline, and pergolide.

It is understood that compounds of the present invention may exist as stereoisomers. Embodiments of the present invention include all enantiomers, diastereomers, and mixtures thereof. Preferred embodiments are predominantly one diastereomer. More preferred embodiments are predominantly one enantiomer.

A particular diastereomer of a compound of formula I represented by a compound of formula Ia

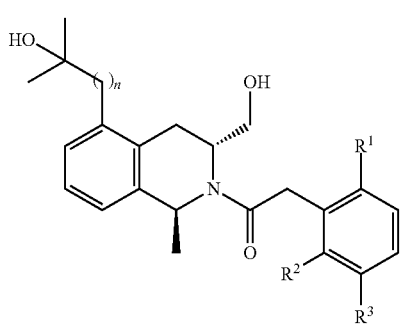

Ia where the dashed bond ⋯⋯ and wedge bond ◢ represent a diastereomer of trans configuration is preferred.

A particular enantiomer of a compound of formula I or Ia represented by Examples including the compound of Example 1: 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone is more preferred.

As used herein, the term "cocrystal" refers to a multiple component crystalline solid form comprising two compounds where the association of compounds is primarily through non-covalent and non-ionic chemical interactions such as hydrogen bonding. In the pharmaceutical arts, a cocrystal typically comprises a first compound which is an active pharmaceutical ingredient and a second compound which is referred to as a guest compound or coformer. A cocrystal may be distinguished from a crystalline salt form in that the first compound remains essentially uncharged or neutral. A cocrystal may be distinguished from a crystalline hydrate or solvate form in that the guest compound is not exclusively water or a solvent. A preferred cocrystal is one of stable form having a suitable melting point.

As used herein, the group "halogen" refers to chloro, fluoro, bromo or iodo. Particular values of halogen are chloro and fluoro.

As used herein, the group "C1-C3 alkoxy" refers to methoxy, ethoxy, n-propoxy and i-propoxy. A particular value of C1-C3 alkoxy is methoxy.

As used herein, the group "C1-C3 alkyl" refers to methyl, ethyl, n-propyl and i-propyl. A particular value of C1-C3 alkyl is methyl.

As used herein, the term "patient" refers to an animal such as a mammal and includes a human. A human is a preferred patient.

It is also recognized that one skilled in the art may treat Parkinson's disease by administering to a patient presently displaying symptoms an effective amount of the compound of formula I. Thus, the terms "treatment" and "treating" are intended to refer to all processes wherein there may be a slowing, interrupting, arresting, controlling, or stopping of the progression of an existing disorder and/or symptoms thereof, but does not necessarily indicate a total elimination of all symptoms.

It is also recognized that one skilled in the art may treat Parkinson's disease by administering to a patient at risk of future symptoms an effective amount of the compound of formula I and is intended to include prophylactic treatment of such.

As used herein, the term "effective amount" of a compound of formula I refers to an amount, that is a dosage, which is effective in treating a disorder, such as Parkinson's disease described herein. The attending diagnostician, as one skilled in the art, can readily determine an effective amount by the use of conventional techniques and by observing results obtained under analogous circumstances. In determining an effective amount or dose of a compound of formula I, a number of factors are considered, including, but not limited to the compound of formula I to be administered; the co-administration of other agents, if used; the species of mammal; its size, age, and general health; the degree of involvement or the severity of the disorder, such as Parkinson's disease; the response of the individual patient; the mode of administration; the bioavailability characteristics of the preparation administered; the dose regimen selected; the use of other concomitant medication; and other relevant circumstances.

A compound of formula I can be administered alone or in the form of a pharmaceutical composition with pharmaceutically acceptable carriers, diluents or excipients. Such pharmaceutical compositions and processes for making the same are known in the art (See, e.g., Remington: The Science and Practice of Pharmacy, D. B. Troy, Editor, 21st Edition., Lippincott, Williams & Wilkins, 2006).

Human D1 Receptor Positive Allosteric Modulation Assay

HEK293 cells stably expressing the human D1 receptor are generated via retroviral gene transduction using the pBABE-bleo vector and the Phoenix retroviral system. The cells are grown in DMEM/F12 (Gibco) supplemented with 10% calf serum, 20 mM HEPES, 2 mM glutamate, and 150 µg/ml zeocin at 37 C in 5% $CO_2$. At approximately 80% confluency, the cells are harvested using 0.25% trypsin/EDTA, suspended in FBS plus 8% DMSO, and stored in liquid nitrogen. On the day of the assay, cells are thawed and re-suspended in STIM buffer (Hanks Balanced Salt Solution supplemented with 0.1% BSA, 20 mM HEPES, 200 µM IBMX, and 100 µM ascorbic acid). A test compound is serially diluted (1:3) in DMSO and then further diluted 1:40 into STIM buffer containing 2× an $EC_{20}$ concentration of dopamine. An $EC_{20}$ concentration of dopamine is defined as the concentration that increases cyclic AMP up to 20% of the maximum amount that can be induced by dopamine; in this assay, the $EC_{max}$ is 5 µM, and the $EC_{20}$ is generally 12 nM. Twenty-five µl of this solution is mixed with 25 µl of cell suspension (1,250 cells) and dispensed into each well of 96-well, half-area plates; the final DMSO concentration is 1.25%. Plates are incubated at 25° C. for 60 min cAMP production is quantified using HTRF detection (Cisbio™) as per vendor instructions: lysis buffer containing anti-cAMP cryptate and D2-conjugate (25 µl of each) are added to the wells, plates are incubated for another 60-90 min, and fluorescence is detected using an EnVision plate reader (PerkinElmer™). Data are converted to cAMP concentrations using a cAMP standard curve, and analyzed as an absolute $EC_{50}$ using a 4-parameter nonlinear logistic equation (Abase™ v5.3.1.22). The absolute $EC_{50}$ for a positive allosteric modulator is calculated as the concentration generating a half-maximal amount of cAMP, based on a window ranging from the dopamine $EC_{20}$, which defines the minimum response, to the $EC_{max}$ response, defined by the addition of 5 µM dopamine.

In the above assay, the compounds exemplified herein demonstrate an absolute $EC_{50}$ less than 300 nM at the human D1 receptor. The compound of Example 1 exhibits an absolute $EC_{50}$ of 3.66±0.67 nM (SEM; n=9) with a maximum response of 83.8±4.4% at the human D1 receptor. The cocrystal of Example 2 exhibits an absolute $EC_{50}$ of 1.11±0.11 nM (SEM; n=2) at the human D1 receptor. The compound of Example 3 exhibits an absolute $EC_{50}$ of 11.75±1.27 nM (SEM; n=16) with a maximum response of 91.3±2.4% at the human D1 receptor. These data demonstrate that exemplified compounds of formula I are positive allosteric modulators of the human D1 receptor.

Anti-Parkinson effects of compounds of the invention can be determined using procedures well known in the art such as animal models of locomotor activity including effects on basal (habituated) locomotor activity and on reserpine-induced akinesia in humanized dopamine 1 receptor (D1) knock-in mice.

Generation of Human D1 Receptor Knock-In Mouse

A transgenic mouse in which the murine dopamine 1 (D1) receptor is replaced by its human counterpart may be generated by standard techniques. For example, mouse genomic fragments are subcloned from the RP23 bacterial artificial chromosome library and recloned into a PGK-neo targeting vector. The mouse open reading frame is replaced with the human D1 receptor open reading frame in exon 2. A neo selection marker upstream of exon 2 is flanked by frt sites for later removal. The flanking of exon 2 by loxP selection sites allows for the option to generate D1 knock-out mice by crossing with mice expressing the cre nuclease gene.

The C57BL/6 N embryonic stem cell line B6-3 is grown on a mitotically inactivated feeder layer of mouse embryonic fibroblasts in high-glucose DMEM with 20% fetal bovine serum and $2 \times 10^6$ unit/1 leukemia inhibitory factor. Ten million embryonic stem cells plus 30 micrograms of linearized vector DNA are electroporated and subjected to G418 selection (200 micrograms/ml). Clones are isolated and analyzed by Southern blotting.

A clone containing the expected size insert is inserted into blastocysts and the resulting mice are genotyped by PCR. A male chimera is crossed with a female containing the Flp nuclease gene to eliminate the selection marker. Progeny containing the human D1 receptor without the selection marker are identified by PCR. A male heterozygote is mated with female C57BL/6 mice. Male and female progeny containing the human D1 receptor are mated and homozygotes are identified by PCR. Behavior and reproduction of the homozygotes is normal, and the colony is maintained in the homozygote state for succeeding generations.

Basal (Habituated) Locomotor Activity

Locomotor activity is measured using an automated system to track movement in mice. Human D1 receptor knock-in mice are placed in chambers and allowed to habituate to the chambers for 60 mins. During this time, they show reduced locomotion over time. Following administration of a compound of the invention, animal movement is increased in a dose-dependent fashion.

More specifically, locomotor activity boxes are situated in rectangular frames with infrared beams for measurement of motor activity (horizontal and vertical activity) called ambulations. Locomotor activity is recorded between time of 7:30 and 15:00 hours.

Mice are randomly assigned to treatment groups as shown in Table 1. Each mouse is placed individually into one of the locomotor activity boxes for 60 minutes habituation. Mice are then dosed orally and total number of ambulations is recorded per 10 minutes for each mouse over a 60 minutes period. In mice with reserpine pretreatment, no previous habituation period is included. Thus, immediately after dosing, the total number of ambulations is measured for 60 minutes. Data is transferred from the software/computers to spreadsheets for further analysis. Statistical analysis is carried out using one-way ANOVA followed by post-hoc analysis using Fishers' LSD or Dunnett's test.

In the basal (habituated) locomotor assay, the compounds of Example 1, 2, 3, 4 and 13 facilitate movement in mice in a dose responsive manner (Tables 1 to 5). This demonstrates the compounds of Example 1, 2, 3, 4 and 13 are effective in locomotor activation of animals that are habituated to the environment.

TABLE 1

| Test Compound | Basal Locomotor Activity (Total Ambulations for 60 min) (Means, SEM, % SE) | |
|---|---|---|
| Vehicle | Means | 542 |
| (20% hydroxypropyl | SEM | 111 |
| betacyclodextrin) | % SE | 30 |
| Example 1 (1 mg/kg) | Means | 542 |
| | SEM | 52 |
| | % SE | 10 |
| Example 1 (3 mg/kg) | Means | 1118 * |
| | SEM | 289 |
| | % SE | 26 |
| Example 1 (6 mg/kg) | Means | 1818 ** @ |
| | SEM | 392 |
| | % SE | 22 |
| Example 1 (10 mg/kg) | Means | 3047 *** @ |
| | SEM | 306 |
| | % SE | 10 |
| Example 1 (30 mg/kg) | Means | 4623 *** @ |
| | SEM | 486 |
| | % SE | 11 |

* $p < 0.05$,  $p < 0.01$, * $p < 0.001$ compared to vehicle (unpaired t-test)
@ $p < 0.01$ compared to vehicle
One-way ANOVA Dunnett's Multiple Comparison Test

TABLE 2

| Test Compound | Basal Locomotor Activity (Total Ambulations for 60 min) (Means, SEM, % SE) | |
|---|---|---|
| Vehicle, n = 8 | Means | 380 |
| (20% hydroxypropyl | SEM | 84 |
| betacyclodextrin) | % SE | 22 |
| Example 2 (3 mg/kg) | Means | 861 ** |
| n = 8 | SEM | 145 |
| | % SE | 17 |
| Example 2 (6 mg/kg) | Means | 1940 ** @ |
| n = 8 | SEM | 456 |
| | % SE | 24 |
| Example 2 (10 mg/kg) | Means | 3539 *** @ |
| n = 8 | SEM | 259 |
| | % SE | 7 |
| Example 2 (20 mg/kg) | Means | 5070 *** @ |
| n = 8 | SEM | 287 |
| | % SE | 6 |
| Example 2 (30 mg/kg) | Means | 4628 *** @ |
| n = 8 | SEM | 374 |
| | % SE | 8 |

$p < 0.01$, * $p < 0.001$ compared to vehicle (unpaired t-test)
@ $p < 0.0001$ compared to vehicle
One-way ANOVA Dunnett's Multiple Comparison Test

TABLE 3

| Test Compound | Basal Locomotor Activity (Total Ambulations for 60 min) (Means, SEM, % SE) | |
|---|---|---|
| Vehicle, n = 8 | Means | 347 |
| (20% hydroxypropyl | SEM | 88 |
| betacyclodextrin) | % SE | 25 |
| Example 3 (3 mg/kg) | Means | 927 * |
| n = 8 | SEM | 183 |
| | % SE | 20 |
| Example 3 (6 mg/kg) | Means | 2180 ** @ |
| n = 8 | SEM | 455 |
| | % SE | 24 |

TABLE 3-continued

| Test Compound | | Basal Locomotor Activity (Total Ambulations for 60 min) (Means, SEM, % SE) | |
|---|---|---|---|
| Example 3 (10 mg/kg) | Means | 2707 | *** @ |
| n = 8 | SEM | 414 | |
|  | % SE | 15 | |
| Example 3 (20 mg/kg) | Means | 3698 | *** @ |
| n = 8 | SEM | 298 | |
|  | % SE | 8 | |
| Example 3 (30 mg/kg) | Means | 3825 | *** @ |
| n = 8 | SEM | 248 | |
|  | % SE | 6 | |

\* $p < 0.01$, \*\* $p < 0.001$, \*\*\* $p < 0.0001$ compared to vehicle (unpaired t-test)
@ $p < 0.0001$ compared to vehicle
One-way ANOVA Dunnett's Multiple Comparison Test

TABLE 4

| Test Compound | | Basal Locomotor Activity (Total Ambulations for 60 min) (Means, SEM, % SE) | |
|---|---|---|---|
| Vehicle, n = 8 | Means | 394 | |
| (20% hydroxypropyl | SEM | 96 | |
| betacyclodextrin) | % SE | 24 | |
| Example 4 (3 mg/kg) | Means | 546 | |
| n = 8 | SEM | 90 | |
|  | % SE | 16 | |
| Example 4 (6 mg/kg) | Means | 665 | |
| n = 8 | SEM | 289 | |
|  | % SE | 43 | |
| Example 4 (10 mg/kg) | Means | 2102 | \* @ |
| n = 8 | SEM | 443 | |
|  | % SE | 21 | |
| Example 4 (20 mg/kg) | Means | 4536 | *** @ |
| n = 8 | SEM | 233 | |
|  | % SE | 5 | |
| Example 4 (30 mg/kg) | Means | 6726 | *** @ |
| n = 8 | SEM | 610 | |
|  | % SE | 9 | |

\* $p < 0.01$, \*\*\* $p < 0.0001$ compared to vehicle (unpaired t-test)
@ $p < 0.0001$ compared to vehicle
One-way ANOVA Dunnett's Multiple Comparison Test

TABLE 5

| Test Compound | | Basal Locomotor Activity (Total Ambulations for 60 min.) (Means, SEM, % SE) | |
|---|---|---|---|
| Vehicle, n = 8 | Means | 305 | |
| (20% hydroxypropyl | SEM | 61 | |
| beta cyclodextrin) | % SE | 20 | |
| Example 13 (3 mg/kg) | Means | 745 | \* |
| n = 8 | SEM | 143 | |
|  | % SE | 19 | |
| Example 13 (6 mg/kg) | Means | 1487 | *** @ |
| n = 8 | SEM | 207 | |
|  | % SE | 14 | |
| Example 13 (10 mg/kg) | Means | 3006 | *** @ |
| n = 8 | SEM | 377 | |
|  | % SE | 13 | |
| Example 13 (20 mg/kg) | Means | 4900 | *** @ |
| n = 8 | SEM | 408 | |
|  | % SE | 8 | |
| Example 13 (30 mg/kg) | Means | 4708 | *** @ |
| n = 8 | SEM | 369 | |
|  | % SE | 8 | |

\* $p < 0.01$,
\*\*\* $p < 0.0001$ compared to vehicle (unpaired t-test)
@ $p < 0.0001$ compared to vehicle
One-way ANOVA Dunnett's Multiple Comparison Test Reversal of Reserpine-Induced Akinesia Reserpine is a catecholamine depleting agent (depletes dopamine and norepinephrine). After 18-24 hours, mice treated with reserpine become akinetic and have reduced locomotor activity counts. Reserpine-induced akinesia is assessed by measuring the effect of compounds on locomotor activity approximately 18-24 hours after a single dose of 0.15, 0.3 mg/kg or 0.6 mg/kg reserpine subcutaneous. The equipment used is the same as that used for habituated locomotor activity for the evaluation of Example 1 in Tables 6 and 7. For the compound of Example 3 (as shown in Table 8), an Ethovision 8 video tracking system is used to measure locomotor activity.

Male humanized dopamine D1 receptor knock-in mice are randomly assigned to treatment groups. Each mouse is placed individually into one of the locomotor activity boxes. Ambulations per 10 minutes for each mouse are measured for up to 60 mins after dosing. Thus, effects on reserpine-induced exploratory behavior are assessed for a total of 60 minutes. Data is transferred from the software/computers to spreadsheets for further analysis. Statistical analysis is carried out using one-way ANOVA followed by post-hoc analysis using t-test.

In the above assay, the compound of Example 1 reverses the effects of reserpine treatment and restores movement in mice in a dose responsive manner as measured by infrared beams (Tables 6 and 7). This demonstrates that the compound of Example 1 is effective in an in vivo model of Parkinson's disease.

TABLE 6

| Test Compound | | Locomotor Activity (Total Ambulations for 60 min.) (Means, SEM, % SE) | |
|---|---|---|---|
| Vehicle Control | Means | 1629 | |
| (20% hydroxypropyl | SEM | 188 | |
| betacyclodextrin, | % SE | 12 | |
| no reserpine) | | | |
| Vehicle + Reserpine | Means | 1336 | |
| (0.15 mg/kg) | SEM | 191 | |
|  | % SE | 14 | |
| Vehicle + Reserpine | Means | 640 | |
| (0.3 mg/kg) | SEM | 61 | |
|  | % SE | 9 | |
| Example 1 | Means | 4623 | *** |
| (10 mg/kg) + Reserpine | SEM | 486 | |
| (0.15 mg/kg) | % SE | 11 | |
| Example 1 | Means | 6222 | *** |
| (30 mg/kg) + Reserpine | SEM | 659 | |
| (0.15 mg/kg) | % SE | 11 | |
| Example 1 | Means | 4056 | *** |
| (30 mg/kg) + Reserpine | SEM | 548 | |
| (0.3 mg/kg) | % SE | 13 | |

\*\*\* $p < 0.001$ compared to vehicle (unpaired t-test)
@ $p < 0.01$ compared to vehicle
One-way ANOVA Dunnett's Multiple Comparison Test

TABLE 7

| Test Compound | | Locomotor Activity (Total Ambulations for 60 min.) (Means, SEM, % SE) | |
|---|---|---|---|
| Vehicle Control, n = 8 | Means | 1545 | |
| (20% hydroxypropyl | SEM | 235 | |
| betacyclodextrin, | % SE | 15 | |
| no reserpine) | | | |
| Vehicle + Reserpine | Means | 813 | @ |
| (0.3 mg/kg) | SEM | 198 | |

TABLE 7-continued

| Test Compound | Locomotor Activity (Total Ambulations for 60 min.) (Means, SEM, % SE) | |
|---|---|---|
| n = 8 | % SE | 24 |
| Example 1 (3 mg/kg) + Reserpine (0.3 mg/kg) | Means | 1107 |
|  | SEM | 265 |
| n = 8 | % SE | 24 |
| Example 1 (6 mg/kg) + Reserpine (0.3 mg/kg) | Means | 1740 * |
|  | SEM | 228 |
| n = 8 | % SE | 13 |
| Example 1 (10 mg/kg) + Reserpine (0.3 mg/kg) | Means | 3042 * @ |
|  | SEM | 300 |
| n = 8 | % SE | 10 |
| Example 1 (30 mg/kg) + Reserpine (0.3 mg/kg) | Means | 4061 * @ |
|  | SEM | 268 |
| n = 8 | % SE | 7 |

@ $p < 0.0001$ compared to vehicle (unpaired t-test)
* $p < 0.0001$ compared to Reserpine (unpaired t-test)

In the above assay, the compound of Example 3 reverses the effects of reserpine treatment and restores movement in mice in a dose responsive manner as measured by video tracking (Table 8). This demonstrates that the compound of Example 3 is effective in an in vivo model of Parkinson's disease.

TABLE 8

| Test Compound | Locomotor Activity (mean distance moved (cm) in 60 min) (Means, SEM, % SE) | |
|---|---|---|
| Vehicle Control, n = 7, (20% hydroxypropyl betacyclodextrin no reserpine) | Means | 9553 |
|  | SEM | 918 |
| Vehicle + Reserpine (0.6 mg/kg) n = 7 | Means | 4990 # |
|  | SEM | 271 |
| Example 3 (3 mg/kg) + Reserpine (0.6 mg/kg) N = 8 | Means | 10243 ** |
|  | SEM | 1351 |
| Example 3 (10 mg/kg) + Reserpine (0.6 mg/kg) n = 8 | Means | 22341 *** |
|  | SEM | 2013 |
| Example 3 (30 mg/kg) + Reserpine (0.6 mg/kg) n = 7 | Means | 26513 *** |
|  | SEM | 3359 |

** $p < 0.01$,
*** $p < 0.001$ compared to reserpine-vehicle
$p < 0.05$, compared to vehicle-vehicle Effects on Extracellular Levels of Acetylcholine in the Prefrontal Cortex Acetylcholine (Ach) is a key brain neurotransmitter for higher cognitive functions. In Alzheimer's disease there is a degeneration of cortical brain areas of importance for memory function such as the hippocampus with loss of cholinergic neurons. Donepezil (Aricept®) is an acetylcholine esterase inhibitor which elevates brain levels of acetylcholine and shows clinical evidence of enhanced cognition. Dopamine D1 agonists have been shown to modulate acetylcholine release and cognitive performance in animal models. Compounds which increase extracellular levels of Ach in the hippocampus of freely moving humanized dopamine D1 receptor knock-in (hD 1 KI) mice are believed to be useful the treatment of cognitive dysfunction associated with Alzheimer's disease.

Experimental Procedure

Microdialysis probes were implanted stereotaxically under isoflurane anaesthesia into the ventral hippocampus (HPC) of male hD1 KI mice (Charles River, U.K). The coordinates from bregma for probe implantation are: AP −3.1; LM+2.8; DV −4.5 mm The following day, animals are connected to allow the probes to be perfused with artificial CSF (containing NaCl (141 mM), KCl (5 mM), $MgCl_2$ (0.8 mM) and $CaCl_2$ (1.5 mM)). Following a 90 minute washout period, dialysate samples are collected at 20 minute intervals. After two hours, animals are injected orally with either vehicle (20% hydroxypropyl betacyclodextrin) or test compound, and samples are collected for a further 3 hours. All samples are frozen immediately on dry-ice and stored at −80° C. pending analysis for a range of neurotransmitters and metabolites.

Sample Analysis

To each dialysis sample (29 μL) is added: 20 μL buffer (1M Bis-Tris, pH10), 20 μL mixed deuterated standard and 260 μl 0.1% w/v dansyl chloride (in acetone). The samples are vortexed and heated at 65° C. for 30 mM, then dried under $N_2$ and re-suspended in 40 μl 50:50 (v/v) ACN:water (containing 10 mM ammonium formate and 0.06% formic acid). The samples are then centrifuged at 13000 rpm for 10 mM at ambient temperature and 35 μl pipetted into 03-FIVR vials; 10 μl is injected onto the LC-MS/MS using a CTC PAL HTC-xt Autosampler.

Chromatographic separation of dansylated samples (including drug standards) is performed under a gradient using Shimadzu LC-20AD XR binary pumps and a 2.6 μm Phenomenex Kinetex, XB-C18 HPLC column Mobile phase A consists of acetonitrile/water 5%:95% (v/v), 2 mM ammonium formate and 0.06% formic acid, and mobile phase B, acetonitrile/water 95%: 5% (v/v), 2 mM ammonium formate and 0.06% formic acid. An AB Sciex API5500 is operated in two periods, period 1, positive TIS mode for detection of acetylcholine (Ach), and period 2 with positive and negative TIS modes.

Data Handling

Data is expressed as a percentage of a pre-injection control period—obtained by averaging the three samples prior to drug delivery (=100%) and expressing values as a percentage of this value. Statistical analyses are undertaken using RM/Fit (ANOVA with Repeated Measures), to compare responses between treatment groups. A probability value of $p<0.05$ is considered statistically significant.

Results

The ACh response is calculated by measuring the Area Under the Curve (AUC), relative to a pre-injection control baseline, for each drug condition over a two hour period post drug administration. Data is then analyzed by ANOVA (One-way; JMP v9) followed by post hoc t-test.

Administration of the compound of Example 4 at 30 mg/kg IP or the acetylcholine esterase inhibitor donepezil at 1 mg/kg, IP, produce a statistically significant increase compared to vehicle controls in extracellular levels of Ach (Table 9). This demonstrates that the compound of Example 4 is effective in an in vivo model of Alzheimer's disease.

TABLE 9

Effect of Example 4 (30 mg/kg IP) or Donepezil (1 mg/kg IP) on ACh response in the hD1 KI mouse hippocampus.

| Test Compound | Response AUC ± SEM (2 hr) |
|---|---|
| Vehicle | 681 ± 51 |
| Example 4 | 1794 ± 476 ## |
| Donepezil | 1472 ± 120 # |

$P < 0.05$,
$P < 0.01$ versus Vehicle;
*** $P < 0.0001$ versus Vehicle, Donepezil and Example 4 (n = 3-4 per group)

Compounds of formula I, which includes compounds of formulas Ia, Ib, and Ic, may be prepared by processes known in the chemical arts or by a novel process described herein. A process for the preparation of a compound of formula I and novel intermediates for the manufacture of a compound of formula I, provide further features of the invention and are illustrated by the following procedures.

Generally, a compound of formula Ia where n is 0, 1 or 2 may be prepared from a compound of formula II where n is 0, 1 or 2 and Pg1 represents a suitable hydroxyl protecting group (Scheme 1). Particular values of Pg1 include tert-butyl(dimethyl)silyl and tert-butyl(diphenyl)silyl. More specifically, a compound of formula II where Pg1 is tert-butyl(dimethyl)silyl is reacted with tetrabutylammonium fluoride in a solvent such as tetrahydrofuran to provide a compound of formula Ia.

Scheme 1

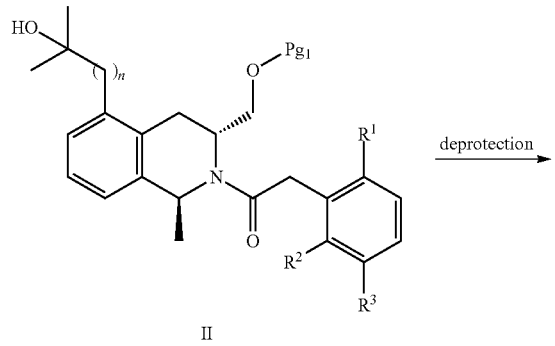

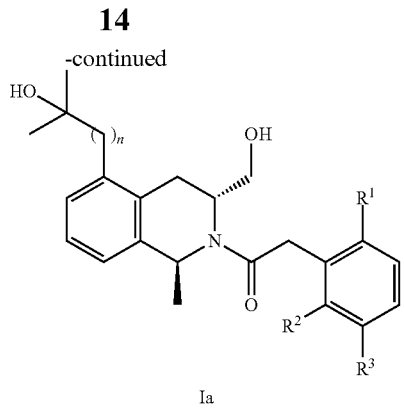

Ia

A compound of formula II where n is 2 and Pg1 is tert-butyl(dimethyl)silyl may be prepared by reacting a compound of formula III with a methyl lithium in a suitable solvent (Scheme 2). Suitable solvents include tetrahydrofuran. A compound of formula III where Pg1 is tert-butyl(dimethyl)silyl may be prepared by reacting a compound of formula IV with hydrogen in the presence of a suitable transition metal catalyst such as 1,1'-bis(di-i-propylphosphino)ferrocene(1,5-cyclooctadiene)rhodium(I) tetrafluoroborate. The reaction is conveniently carried out in a solvent such as methanol. A compound of formula IV where Pg1 is tert-butyl (dimethyl)silyl may be prepared by reacting a compound of formula V with ethyl acrylate in the presence of a transition metal coupling catalyst such as palladium acetate, a ligand such as tri-o-tolylphosphine and a base such as triethyamine. The reaction is conveniently carried out in a solvent such as acetonitrile. A compound of formula V may be prepared by acylating a compound of formula VIII with the appropriate $R^1$, $R^2$, $R^3$-phenylacetic acid in the presence of an activating agent such as benzotriazol-1-yl-oxytripyrrolidinophosphonium hexafluorophosphate and a base such as triethyl amine. The reaction is conveniently carried out in a solvent such as dimethyl formamide.

Scheme 2

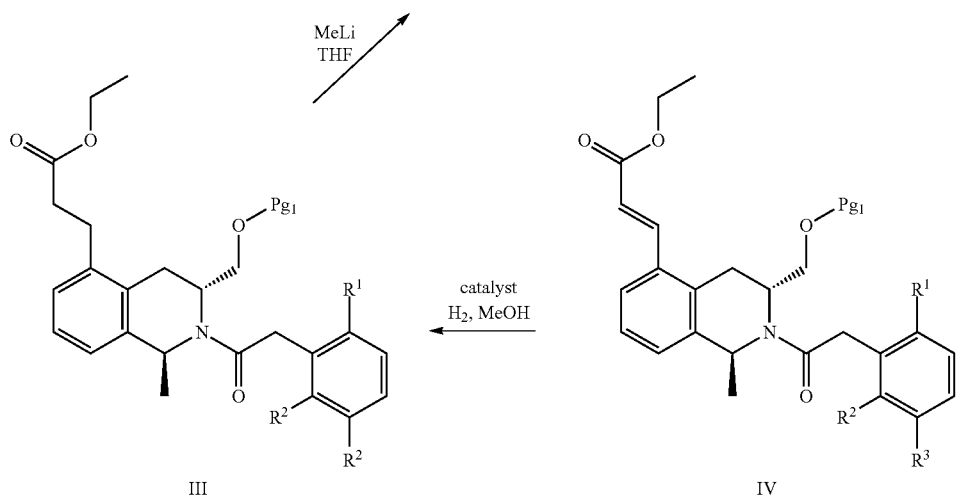

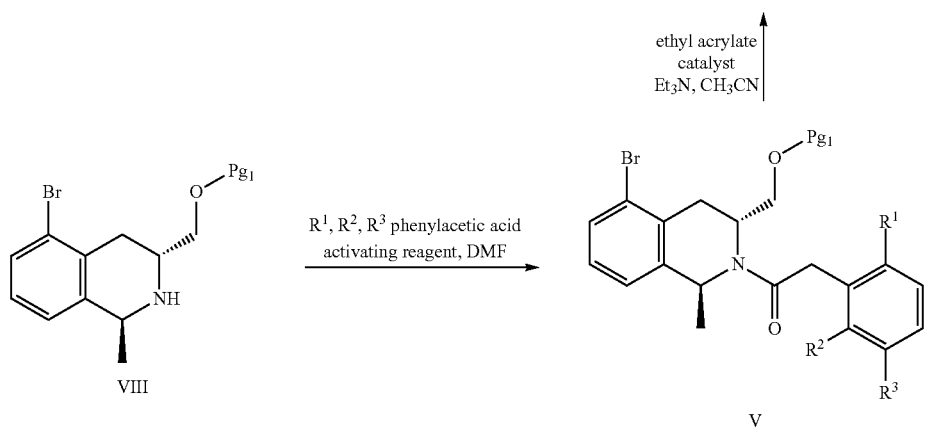

Alternatively, a compound of formula II may be prepared from a compound of formula VI where Pg1 is a suitable hydroxyl protecting group (Scheme 3). Particular values of Pg1 include tert-butyl(dimethyl)silyl and tert-butyl(diphenyl)silyl. More specifically, a compound of formula VI where Pg1 is tert-butyl(dimethyl)silyl is acylated with 2,6-dichlorophenylacetic acid in the presence of an activating agent such as 1,1'-carbonyldiimidazole to provide a compound of formula II. The reaction is conveniently carried out in a solvent such as tetrahydrofuran. A compound of formula VI may be prepared by reducing a compound of formula VII with hydrogen in the presence of a catalyst such as palladium. The reaction is conveniently carried out in a solvent such as ethanol. A compound of formula VII may be prepared by coupling a compound of formula VIII with 2-methylbut-3-en-2-ol in the presence of a catalyst such as palladium acetate, a ligand such as 2-dicyclohexylphosphino-2',6'-dimethoxybiphenyl and a base such potassium carbonate. The reaction is conveniently carried out in a solvent such as dimethylformamide. A compound of formula VIII may be prepared in a multistep fashion from a compound of formula X through an intermediate compound of formula IX as known in the chemical arts or by a process described in the Preparations and Examples. A compound of formula X may be prepared as described in the Preparations and Examples.

Scheme 3

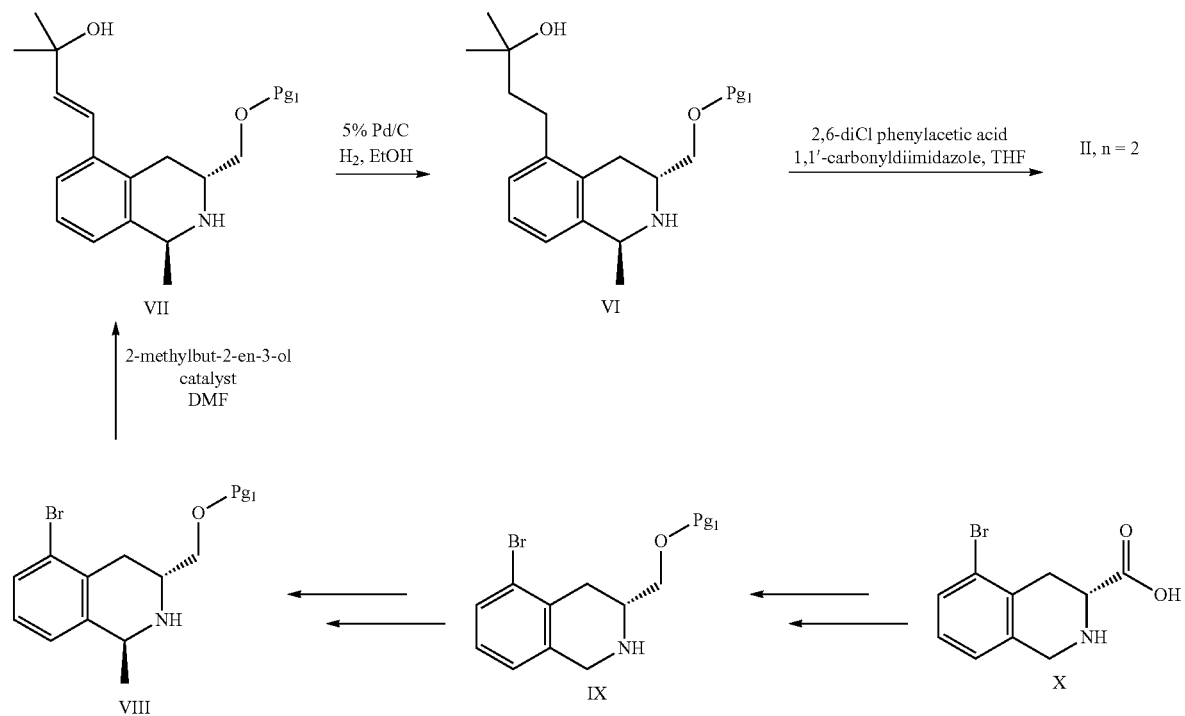

A compound of formula II where n is 0 and Pg1 is tert-butyl(dimethyl)silyl may be prepared by reacting a compound of formula IIIa with methyl magnesium bromide in a suitable solvent (Scheme 4). A compound of formula IIIa may be prepared by acylating a compound of formula VIIa with the appropriate $R^1$, $R^2$, $R^3$-phenylacetic acid in the presence of an activating agent such as benzotriazol-1-yl-oxytripyrrolidinophosphonium hexafluorophosphate and a base such as triethyl amine. The reaction is conveniently carried out in a solvent such as dimethyl formamide. A compound of formula VIIa may be prepared by reacting a compound of formula VIII with carbon monoxide and methanol in the presence of a palladium (0) catalyst.

Scheme 4

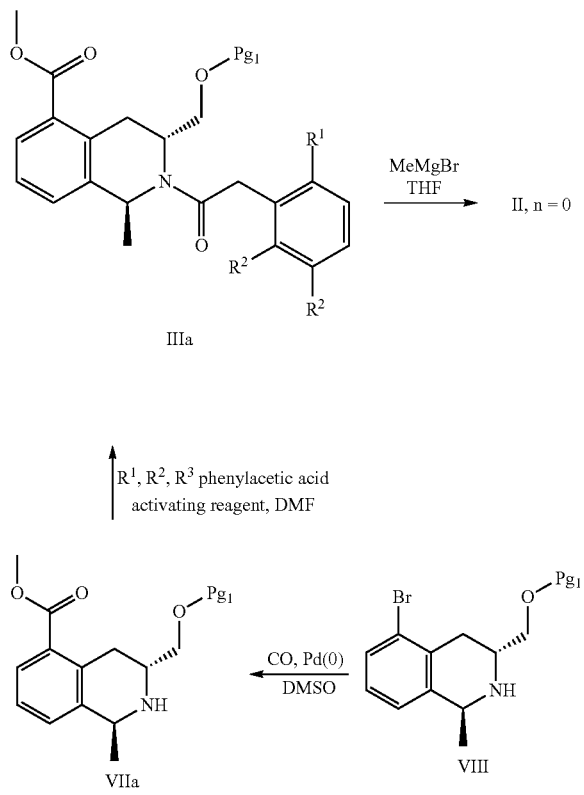

Scheme 5

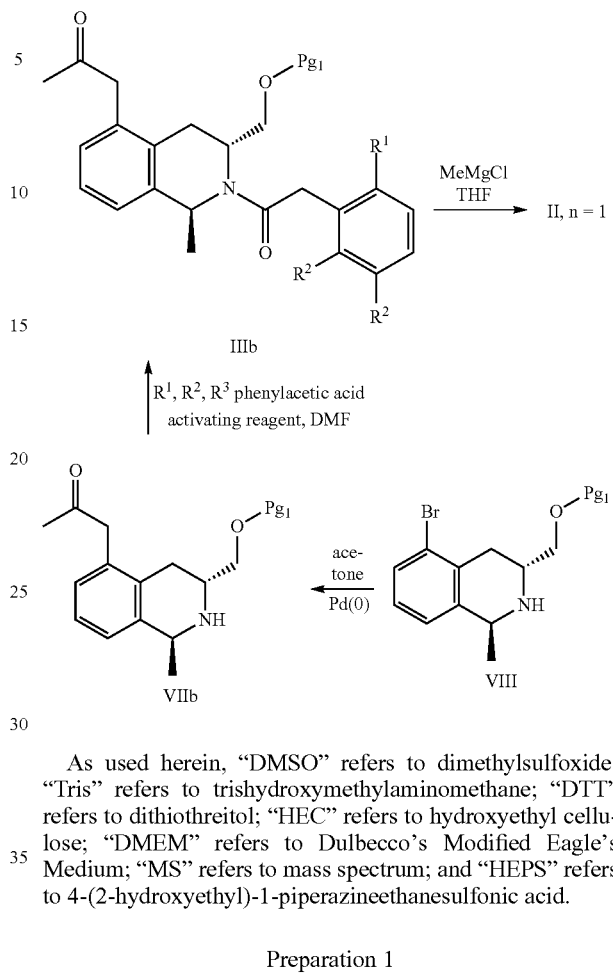

A compound of formula II where n is 1 and Pg1 is tert-butyl(dimethyl)silyl may be prepared by reacting a compound of formula IIIb with methyl magnesium chloride in a suitable solvent (Scheme 5). A compound of formula IIIb may be prepared by acylating a compound of formula VIIb with the appropriate $R^1$, $R^2$, $R^3$-phenylacetic acid in the presence of an activating agent such as benzotriazol-1-yl-oxytripyrrolidinophosphonium hexafluorophosphate and a base such as triethyl amine. The reaction is conveniently carried out in a solvent such as dimethyl formamide. A compound of formula VIIb may be prepared by reacting a compound of formula VIII with acetone in the presence of a palladium (0) catalyst and a ligand as described in the examples and preparations.

As used herein, "DMSO" refers to dimethylsulfoxide; "Tris" refers to trishydroxymethylaminomethane; "DTT" refers to dithiothreitol; "HEC" refers to hydroxyethyl cellulose; "DMEM" refers to Dulbecco's Modified Eagle's Medium; "MS" refers to mass spectrum; and "HEPS" refers to 4-(2-hydroxyethyl)-1-piperazineethanesulfonic acid.

Preparation 1

Synthesis of methyl 2-bromo-D-phenylalaninate hydrochloride

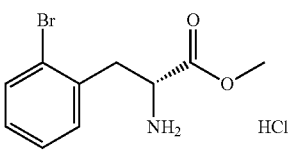

Dissolve 2-bromo-D-phenylalanine (22.4 g, 91.8 mmol) in methanol (459 mL). Add acetyl chloride (65.3 mL, 917.7 mmol) at room temperature. Stir for 36 hours. Concentrate under reduced pressure to give the title compound (27.2 g, 92.3 mmol). MS (m/z): 258 (M+1).

Alternative synthesis of methyl 2-bromo-D-phenylalaninate hydrochloride

Add acetyl chloride (562.79 g, 7.17 mol) to methanol (10.00 L) at 0° C. in an appropriate vessel. Heat the mixture to 17.5° C. and stir. After 30 minutes, add 2-bromo-D-phenylalanine (500.00 g, 2.05 moles) and heat to reflux. After 4 hours, cool to 20° C. and remove the solvent under reduced pressure to give the title compound (589 g, 1.96 mol) as an off-white solid. MS (m/z): 258 (M-Cl ($^{79}$Br)), 260 (M-Cl ($^{81}$Br)).

Preparation 2

Synthesis of methyl 2-bromo-N-(methoxycarbonyl)-D-phenylalaninate

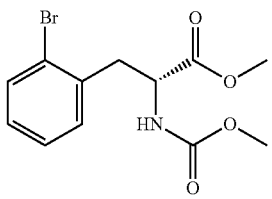 [SMILES: COC(=O)N[C@H](Cc1ccccc1Br)C(=O)OC]

Dissolve methyl 2-bromo-D-phenylalaninate hydrochloride (27.2 g, 92.3 mmol) in dichloromethane (923 mL) and water (185 mL). Add sodium bicarbonate (31.0 g, 369.4 mmol) and methyl chloroformate (7.86 mL, 101.6 mmol) at room temperature. Stir the mixture 2.5 hours. Dilute with water and extract with dichloromethane. Dry the dichloromethane extracts over sodium sulfate, filter, and concentrate under reduced pressure. Purify the residue by silica gel chromatography eluting with ethyl acetate:hexanes (10-75% gradient) to give the title compound (29.1 g, 92.1 mmol). MS (m/z): 316 (M+1).

Alternative synthesis of methyl 2-bromo-N-(methoxycarbonyl)-D-phenylalaninate

Add water (2.94 L) and sodium hydrogen carbonate (648.25 g, 7.64 mol) to methyl 2-bromo-D-phenylalaninate hydrochloride (580 g, 1.91 mol) in dichloromethane (9.86 L) at 10° C. in an appropriate vessel. After 5 minutes add methyl chloroformate (198.53 g, 2.10 mol) and stir the mixture at 20° C. After 3 hours add water (2.5 L) and separate the layers. Extract the aqueous with dichloromethane, dry the combined organic extracts over sodium sulfate and concentrate under reduced pressure to give the title compound (556 g, 1.74 mol). MS (m/z): 315.8 (M+1 ($^{79}$Br)), 317.8 (M+1 ($^{81}$Br)).

Preparation 3

Synthesis of dimethyl (3R)-5-bromo-3,4-dihydro-1H-isoquinoline-2,3-dicarboxylate

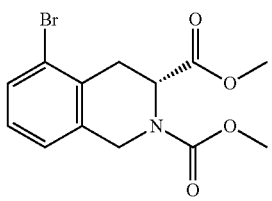 [SMILES: COC(=O)[C@H]1Cc2c(Br)cccc2CN1C(=O)OC]

Stir a mixture of methyl 2-bromo-N-(methoxycarbonyl)-D-phenylalaninate (29.1 g, 92.10 mmol) and paraformaldehyde (9.13 g, 101.3 mmol) in glacial acetic acid (115 mL, 2.01 mol) and concentrated sulfuric acid (38.4 mL, 719.9 mmol) at room temperature for 7 hours. Partition between water and ethyl acetate. Separate the layers and extract the aqueous layer with ethyl acetate. Combine the ethyl acetate extracts and dry over sodium sulfate, filter, and concentrate under reduced pressure. Purify the residue by silica gel chromatography eluting with ethyl acetate: hexanes (5-40% gradient) to give the title compound (27.6 g, 84.0 mmol). MS (m/z): 328 (M+1).

Preparation 3a

Synthesis of dimethyl (3R)-5-bromo-3,4-dihydro-1H-isoquinoline-2,3-dicarboxylate and (3R)-5-bromo-2-methoxycarbonyl-3,4-dihydro-1H-isoquinoline-3-carboxylic acid.

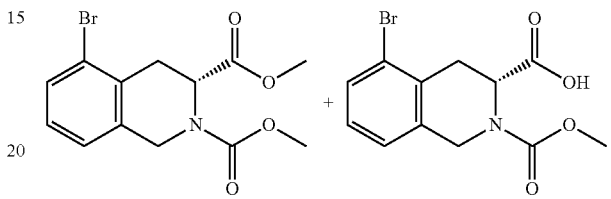

To acetic acid (4.29 L) at 10° C. in an appropriate vessel, add 2-bromo-N-(methoxycarbonyl)-D-phenylalaninate (572 g, 1.81 mol) and paraformaldehyde (205.86 g, 2.17 mol). After 10 minutes slowly add concentrated sulfuric acid (2.63 kg, 26.83 mol) and then stir at 35° C. After 12 hours, cool to 15° C. and add water (7.5 L) and ethyl acetate (6 L). Separate the layers and re-extract the aqueous with ethyl acetate (2.5 L). Dry the combined organic extracts over sodium sulfate, filter and concentrate under reduced pressure to give a mixture of the title compounds with acetic acid (640 g, 1.69 moles). Mass spectrum (m/z): 3a: 327.95 (M+1 ($^{79}$Br)), 330.05 (M+1 ($^{81}$Br)). 3b: 314 (M+1 ($^{79}$Br)), 315.95 (M+1 ($^{81}$Br)).

Preparation 4

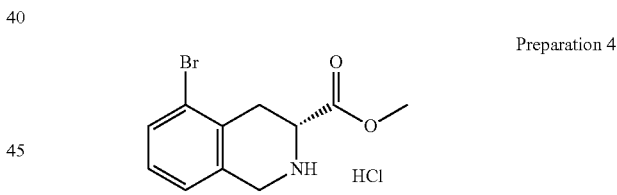

Synthesis of methyl (3R)-5-bromo-1,2,3,4-tetrahydroisoquinoline-3-carboxylate hydrochloride Dissolve dimethyl (3R)-5-bromo-3,4-dihydro-1H-isoquinoline-2,3-dicarboxylate (27.55 g, 84.0 mmol) in 5N hydrochloric acid (330.6 mL, 1.65 mol) and heat to reflux for three days. Concentrate under reduced pressure to give a white solid. Wash the solid with diethyl ether and dry under vacuum at 40° C. overnight to give (3R)-5-bromo-1,2,3,4-tetrahydroisoquinoline-3-carboxylic acid hydrochloride (1:1) (20.8 g, 71.1 mmol). Add acetyl chloride (50.6 mL, 711.0 mmol) to a 0° C. mixture of (3R)-5-bromo-1,2,3,4-tetrahydroisoquinoline-3-carboxylic acid hydrochloride (1:1) (20.8 g, 71.1 mmol) in methanol (474 mL). Warm to room temperature and stir for 36 hours. Concentrate under reduced pressure and dry to give the title compound (21.9 g, 71.4 mmol). MS (m/z): 270 (M+1).

Preparation 5

Synthesis of (3R)-5-bromo-1,2,3,4-tetrahydroisoquinoline-3-carboxylic acid hydrochloride

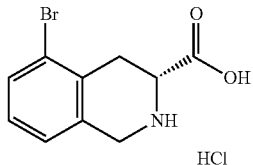 [SMILES: O=C(O)[C@H]1Cc2c(Br)cccc2CN1 ; Cl]

Add water (1.3 L) and 36.5% hydrochloric acid (9.07 Kg, 90.81 moles) to a mixture of dimethyl (3R)-5-bromo-3,4-dihydro-1H-isoquinoline-2,3-dicarboxylate and (3R)-5-bromo-2-methoxycarbonyl-3,4-dihydro-1H-isoquinoline-3-carboxylic acid (Preparation 3a) (520 g, 1.27 moles) in an appropriate vessel and stir the mixture at 95° C. After 12 hours cool the mixture to 10° C. and stir for 15 minutes. Filter the mixture and dry the solid under vacuum at 40° C. give the title compound (332 g, 1.13 moles). MS (m/z): 256.1 (M-Cl ($^{79}$Br)), 258 (M-Cl ($^{81}$Br)).

Preparation 6

Synthesis of 2-tert-butyl-3-methyl-(3R)-5-bromo-3,4-dihydro-1H-isoquinoline-2,3-dicarboxylate

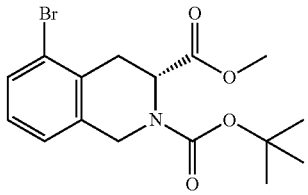 [SMILES: COC(=O)[C@H]1Cc2c(Br)cccc2CN1C(=O)OC(C)(C)C]

Dissolve methyl (3R)-5-bromo-1,2,3,4-tetrahydroisoquinoline-3-carboxylate hydrochloride (21.0 g, 68.5 mmol) in 1,4-dioxane (685 mL). Add saturated sodium bicarbonate solution (685 mL, 17.5 mol) and di-tert-butyldicarbonate (29.9 g, 137.0 mmol) at room temperature. Stir the biphasic mixture for 90 min. Extract with ethyl acetate. Dry the ethyl acetate over sodium sulfate, filter, and concentrate under reduced pressure. Purify the residue by silica gel chromatography eluting with ethyl acetate:hexanes (5-50% gradient) to give the title compound (19.5 g, 52.7 mmol). MS (m/z): 270 (M-tBOC+1).

Preparation 7

Synthesis of [(3R)-5-bromo-1,2,3,4-tetrahydroisoquinolin-3-yl]methanol

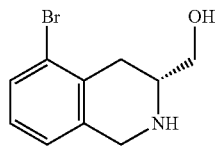 [SMILES: OC[C@H]1Cc2c(Br)cccc2CN1]

Add lithium aluminum hydride (2 L, 2.00 mol, 1M in THF) to (3R)-5-bromo-1,2,3,4-tetrahydroisoquinoline-3-carboxylic acid hydrochloride (325.4 g, 1.11 mol) in tetrahydrofuran (4.88 L) at −35° C. in an appropriate vessel, then warm to 25° C. over 60 minutes and stir. After 3 hours, cool the mixture to −5° C. then add water (76 mL), 15% w/w aqueous sodium hydroxide (76 mL) and water (228 mL). Heat the mixture to 25° C., add anhydrous magnesium sulfate (750 g) and stir. Filter the mixture and concentrate under reduced pressure to give a solid. Add dichloromethane (690 mL) to the solid and slurry for 30 minutes before filtration to give a solid. Dry the solid under vacuum at 35° C. to give the title compound (148.9 g, 0.55 mol). MS (m/z): 242(M+1 ($^{79}$Br)), 244(M+1 ($^{81}$Br)).

Preparation 8

Synthesis of tert-butyl (3R)-5-bromo-3-(hydroxymethyl)-3,4-dihydro-1H-isoquinoline-2-carboxylate

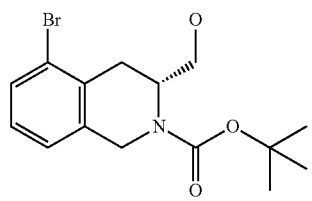 [SMILES: CC(C)(C)OC(=O)N1Cc2cccc(Br)c2C[C@@H]1CO]

Add methanol (10.1 mL, 248.5 mmol) and lithium borohydride (99.4 mL, 198.8 mmol, 2 M in THF) to a solution of 2-tert-butyl-3-methyl-(3R)-5-bromo-3,4-dihydro-1H-isoquinoline-2,3-dicarboxylate (18.4 g, 49.7 mmol) in tetrahydrofuran (497 mL) at room temperature on a water bath. Stir 40 min and quench the reaction with water. Extract with ethyl acetate. Dry the ethyl acetate extracts over sodium sulfate, filter, and concentrate under reduced pressure. Purify the residue by silica gel chromatography eluting with ethyl acetate: hexanes (5-80% gradient). Dry under high vacuum overnight to give the title compound as a white solid (19.1 g, 55.8 mmol). MS (m/z): 286 (M-tBu+1).

Preparation 9

Synthesis of (3R)-5-bromo-3-({[tert-butyl(dimethyl)silyl]oxy}methyl)-1,2,3,4-tetrahydroisoquinoline

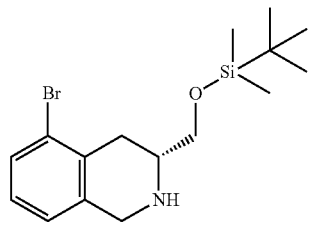 [SMILES: CC(C)(C)[Si](C)(C)OC[C@H]1Cc2c(Br)cccc2CN1]

Add trifluoroacetic acid (75.5 mL, 998.3 mmol) to solution of tert-butyl (3R)-5-bromo-3-(hydroxymethyl)-3,4-dihydro-1H-isoquinoline-2-carboxylate (15.5 g, 45.3 mmol) in dichloromethane (226 mL) at room temperature. Stir 30 min and concentrate under reduced pressure. Dry under vacuum to give [(3R)-5-bromo-1,2,3,4-tetrahydroisoquinolin-3-yl]methanol; 2,2,2-trifluoroacetic acid as a wet solid. Dissolve [(3R)-5-bromo-1,2,3,4-tetrahydroisoquinolin-3-yl]methanol; 2,2,2-trifluoroacetic acid in dichloromethane (753 mL).

Add 1H-imidazole (51.3 g, 753 mmol), N,N-Dimethyl-4-pyridinamine (460 mg, 3.77 mmol), and t-butyldimethylchlorosilane (13.6 g, 90.4 mmol). Stir at room temperature overnight. Add saturated ammonium chloride solution and extract with dichloromethane. Dry the dichloromethane extracts over sodium sulfate, filter, and concentrate under reduced pressure. Combine with the crude product from a substantially same reaction run with 19.4 mmol of tert-butyl (3R)-5-bromo-3-(hydroxymethyl)-3,4-dihydro-1H-isoquinoline-2-carboxylate. Purify the residue by silica gel chromatography eluting with ethyl acetate: hexanes (5-40% gradient) to give the title compound (14.3 g, 40.1 mmol). MS (m/z): 356 (M+1).

Alternative synthesis of (3R)-5-bromo-3-({[tert-butyl(dimethyl)silyl]oxy}methyl)-1,2,3,4-tetrahydroisoquinoline Add tert-butyldimethylchlorosilane (193.7 g, 1.29 mol) to a mixture of [(3R)-5-bromo-1,2,3,4-tetrahydroisoquinolin-3-yl]methanol (148.9 g, 0.58 mol), 1H-imidazole (202.9 g, 2.92 mol), 4-dimethylaminopyridine (0.72 g, 5.84 mmol) and N,N-dimethylformamide (1.04 L) in dichlormethane (2.61 L) at 20° C. and stir in an appropriate vessel. After 3 hours, cool the mixture to 10° C. and add saturated aqueous ammonium chloride solution (1.3 L). Extract the aqueous with dichloromethane and wash the combined organic extracts with brine (2×2 L), dry over anhydrous sodium sulfate and concentrate under reduced pressure to give a residue. Dissolve the residue in methyl tert-butyl ether (1.5 L) and wash with brine (2×1 L). Dilute the organic phase with toluene (5 L) and concentrate under reduced pressure to give a residue. Add toluene (2.6 L) to the residue and concentrate under reduced pressure to give the title compound (210 g, 0.53 mol). MS (m/z). 356(M+1 ($^{79}$Br)), 358(M+1 (81Br)).

Preparation 10

Synthesis of (3R)-5-bromo-3-({[tert-butyl(dimethyl)silyl]oxy}methyl)-3,4 dihydroisoquinoline

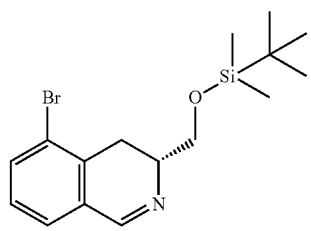 [SMILES: CC(C)(C)[Si](C)(C)OC[C@H]1Cc2c(Br)cccc2C=N1]

Dissolve (3R)-5-bromo-3-({[tert-butyl(dimethyl)silyl]oxy}methyl)-1,2,3,4-tetrahydroisoquinoline (4.2 g, 11.8 mmol) in diethyl ether (118 mL). Add N-chlorosuccinimide (2.36 g, 17.7 mmol). Stir 30 min at room temperature and concentrate under reduced pressure. Dissolve the residue in potassium hydroxide (42.0 mL, 30.3 mmol, 5% in MeOH) and stir for 30 min at room temperature. Pour into water and extract with dichloromethane. Dry the dichloromethane extracts over sodium sulfate, filter, and concentrate under reduced pressure. Purify the residue by silica gel chromatography eluting with ethyl acetate: hexanes (5-100% gradient) to give the title compound (3.40 g, 9.59 mmol). MS (m/z): 354 (M+1).

Alternative synthesis of (3R)-5-bromo-3-({[tert-butyl(dimethyl)silyl]oxy}methyl)-3,4 dihydroisoquinoline Add N-chlorosuccinimide (106.7 g, 0.79 mol) to a solution of (3R)-5-bromo-3-({[tert-butyl(dimethyl)silyl]oxy}methyl)-1,2,3,4-tetrahydroisoquinoline (220 g, 0.52 mol) in tetrahydrofuran (3.85 L) at 20° C. in an appropriate vessel and stir. After 30 minutes concentrate the mixture under reduced pressure and dissolve the residues in 5% w/w potassium hydroxide in methanol (2.2 L, 1.69 moles) and stir at 20° C. After 30 minutes, add the mixture to water (3 L) and extract three times with dichloromethane (3×1 L). Dry the combined organic extracts over anhydrous magnesium sulfate and concentrate under reduced pressure to give the title compound (210 g, 0.50 mol). MS (m/z): 354(M+1 ($^{79}$Br)), 356(M+1 (81Br)).

Preparation 11

Synthesis of (1S,3R)-5-bromo-3-({[tert-butyl(dimethyl)silyl]oxy}methyl)-1-methyl-1,2,3,4-tetrahydroisoquinoline

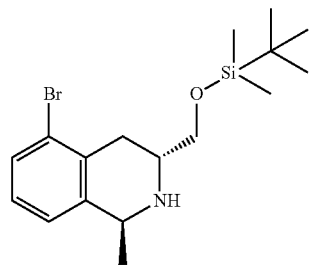 [SMILES: C[C@@H]1N[C@@H](CO[Si](C)(C)C(C)(C)C)Cc2c(Br)cccc21]

Dissolve (3R)-5-bromo-3-({[tert-butyl(dimethyl)silyl]oxy}methyl)-3,4 dihydroisoquinoline (3.4 g, 9.59 mmol) in diethyl ether (160 mL). Cool to −78° C. on a dry ice-acetone bath. Add methylmagnesium chloride (26.9 mL, 80.6 mmol, 3M in THF) dropwise. Warm the reaction mixture slowly to room temperature and stir overnight. Quench with saturated ammonium chloride solution slowly. Extract with dichloromethane and dry over sodium sulfate, filter, and concentrate under reduced pressure. Combine with the crude product from a substantially same reaction run with 1.73 mmol of (3R)-5-bromo-3-({[tert-butyl(dimethyl)silyl]oxy}methyl)-3,4 dihydroisoquinoline. Purify the combined residues by silica gel chromatography eluting with ethyl acetate: hexanes (5-65% gradient) to give the title compound (3.78 g, 10.2 mmol). MS (m/z): 370 (M+1).

The relative configuration of compound (1S,3R)-5-bromo-3-({[tert-butyl(dimethyl)silyl]oxy}methyl)-1-methyl-1,2,3,4-tetrahydroisoquinoline is determined by NMR spectroscopy using one-dimensional NOE experiments (1D-NOESY). Selective excitation of the methyl group at 1.30 ppm gives rise to a NOE for Ha at 3.11 ppm. This NOE enhancement is only consistent with a configuration in which the methyl and Ha are on the same side of the ring (trans isomer) because in the cis isomer the methyl protons are too far away from Ha to show an NOE. Since the absolute chemistry for position 3 is known to be R, then the absolute chemistry at position 1 is deduced to be S.

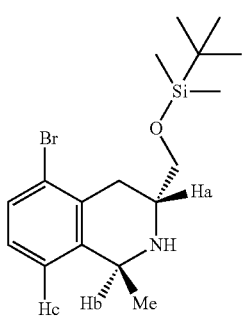

Alternative synthesis of (1S,3R)-5-bromo-3-({[tert-butyl(dimethyl)silyl]oxy}methyl)-1-methyl-1,2,3,4-tetrahydroisoquinoline

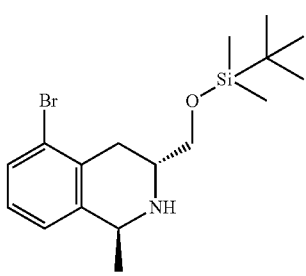 [SMILES: C[C@@H]1N[C@@H](CO[Si](C)(C)C(C)(C)C)Cc2c(Br)cccc21]

Add methylmagnesium chloride (0.66 L, 1.99 mol, 3M in THF) to a solution of (3R)-5-bromo-3-({[tert-butyl(dimethyl)silyl]oxy}methyl)-3,4 dihydroisoquinoline (93.5 g, 0.24 mol) in diethyl ether (2.8 L) at −65° C. in an appropriate vessel. Then heat the reaction mixture to 20° C. over 2 hours and stir. After 16 hours, cool the mixture to 0° C. and quench the reaction with saturated aqueous ammonium chloride solution (2.5 L) and extract with ethyl acetate (2.5 L) and filter the mixture. Wash the combined organic extracts with brine (1 L), dry over anhydrous magnesium sulfate and concentrate under reduced pressure to give the crude title compound as an oil. Combine the oil with crude products from substantially same reactions run with 48 mmol and 229 mmol of [(3R)-5-bromo-3,4-dihydroisoquinolin-3-yl]methoxy-tert-butyl-dimethyl-silane and purify them by silica gel chromatography eluting with ethyl acetate in hexanes (gradient 5-65% ethyl acetate) to give the title compound (151 g, 0.41 mol). MS (m/z): 370.1 (M+1 ($^{79}$Br)), 372.1 (M+1 ($^{81}$Br)).

Preparation 12

Synthesis of tert-butyl (1S,3R)-5-bromo-3-[[tert-butyl(dimethyl)silyl]oxymethyl]-1-methyl-3,4-dihydro-1H-isoquinoline-2-carboxylate

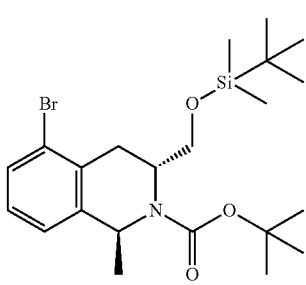 [SMILES: C[C@H]1c2cccc(Br)c2C[C@H](CO[Si](C)(C)C(C)(C)C)N1C(=O)OC(C)(C)C]

Add di-tert-butyl dicarbonate (1.23 g, 5.54 mmol) to a solution of [(1S,3R)-5-bromo-1-methyl-1,2,3,4-tetrahydroisoquinolin-3-yl]methoxy-tert-butyl-dimethyl-silane (2.01 g, 5.43 mmol) in dichloromethane (15 mL). Stir the reaction mixture over night at ambient temperature. Concentrate under reduced pressure. Dissolve the residue in dichloromethane and wash with water and brine, dry over sodium sulfate, filter and concentrate under reduced pressure. Purify by silica gel chromatography eluting with ethyl acetate: hexanes (0-4% gradient) to give the title compound (2.54 g, 5.40 mmol). MS (m/z): 370.2, 372.2 (M-BOC+1).

Preparation 13

Synthesis of 1-1(1S,3R)-5-bromo-3-({[tert-butyl(dimethyl)silyl]oxy}methyl)-1-methyl-3,4-dihydroisoquinolin-2(1H)-yl]-2-(2,6-dichlorophenyl)ethanone.

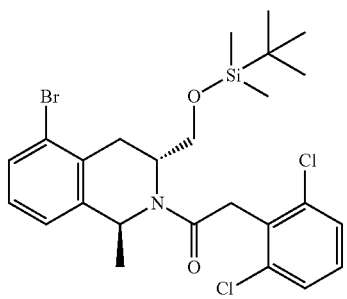 [SMILES: C[C@H]1c2cccc(Br)c2C[C@H](CO[Si](C)(C)C(C)(C)C)N1C(=O)Cc1c(Cl)cccc1Cl]

Add benzotriazol-1-yl-oxytripyrrolidinophosphonium hexafluorophosphate (7.97 g, 15.3 mmol) to a mixture of (1S,3R)-5-bromo-3-({[tert-butyl(dimethyl)silyl]oxy}methyl)-1-methyl-1,2,3,4-tetrahydroisoquinoline (3.78 g, 10.2 mmol) and 2,6-dichlorophenylacetic acid (2.30 g, 11.2 mmol) in dimethylformamide (51.0 mL). Add triethylamine (2.13 mL, 15.3 mmol) and stir at room temperature 3 hours. Dilute with water and extract with dichloromethane. Dry the dichloromethane extracts over sodium sulfate, filter and concentrate under reduced pressure. Purify the residue by silica gel chromatography eluting with ethyl acetate: hexanes (5-50% gradient) to give the title compound (4.70 g, 8.43 mmol). MS (m/z): 556 (M+1).

Preparation 14

Synthesis of ethyl (2E)-3-{(1S,3R)-3-({[tert-butyl(dimethyl)silyl]oxy}methyl)-2-[(2,6-dichlorophenyl)acetyl]-1-methyl-1,2,3,4-tetrahydroisoquinolin-5-yl}prop-2-enoate

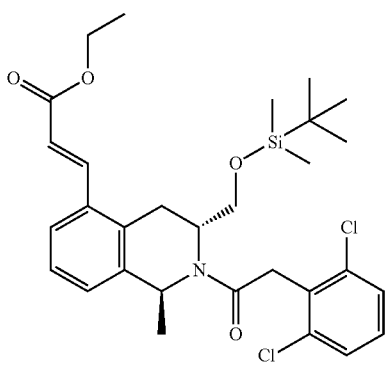 [SMILES: CCOC(=O)/C=C/c1cccc2c1C[C@H](CO[Si](C)(C)C(C)(C)C)N(C(=O)Cc1c(Cl)cccc1Cl)[C@H]2C]

Bubble nitrogen through acetonitrile. Place tri-o-tolylphosphine (72.3 mg, 0.23 mmol), palladium (II) acetate (11.8 mg, 0.052 mmol) and acetonitrile (0.96 mL) in a microwave vessel. Stir 10 min. Add ethyl acrylate (0.31 mL, 2.88 mmol). Add 1-[(1S,3R)-5-bromo-3-({[tert-butyl(dimethyl)silyl]oxy}methyl)-1-methyl-3,4-dihydroisoquinolin-2(1H)-yl]-2-(2,6-dichlorophenyl)ethanone (0.54 g, 0.96 mmol). Add triethylamine (0.40 mL, 2.88 mmol) and stir vigorously. Blow nitrogen across the surface of the reaction. Seal the vessel and heat to 160° C. for 35 min in a microwave. Cool to room temperature and dilute with ethyl acetate. Filter the precipitate and wash with ethyl acetate. Concentrate the filtrate under reduced pressure to give a brown oil. Combine with the crude product from a substantially same reaction run with 0.27 mmol of 1-[(1S,3R)-5-bromo-3-({[tert-butyl(dimethyl)silyl]oxy}methyl)-1-methyl-3,4-dihydroisoquinolin-2(1H)-yl]-2-(2,6-dichlorophenyl)ethanone. Purify the combined residues by silica gel chromatography, eluting with ethyl acetate: hexanes (gradient, 0-10%) to give the title compound (0.54 g, 0.93 mmol). MS (m/z): 576 (M+1). The following compound is prepared essentially by the method of Preparation 14.

Add 10% palladium on carbon (0.09 g) to a 100 ml Parr bottle. Purge with nitrogen. Add ethanol (5 mL) to wet the catalyst. Add tert-butyl (1S,3R)-3-[[tert-butyl(dimethyl)silyl]oxymethyl]-5-[(E)-3-ethoxy-3-oxo-prop-1-enyl]-1-methyl-3,4-dihydro-1H-isoquinoline-2-carboxylate (330 mg, 0.67 mmol) as a solution in ethanol (15 mL). Seal the bottle and purge with nitrogen. Purge the vessel with hydrogen and pressurize to 414 kPa of hydrogen. Shake at room temperature for 1.5 hours. Vent and open the vessel. Filter the reaction mixture. Concentrate the filtrate under reduced pressure. Purify the residue by silica gel chromatography, eluting with ethyl acetate:hexanes (0-10% gradient) to give the title compound as a clear colorless oil (252 mg, 0.51 mmol). MS (m/z): 392.2 (M-BOC+1).

Preparation 17

Synthesis of ethyl 3-{(1S,3R)-3-({[tert-butyl(dimethyl)silyl]oxy}methyl)-2-[(2,6-dichlorophenyl)

| Prep. No. | Chemical name | Structure | Physical data |
|---|---|---|---|
| 15 | tert-butyl (1S,3R)-3-[[tert-butyl(dimethyl)silyl]oxymethyl]-5-[(E)-3-ethoxy-3-oxo-prop-1-enyl]-1-methyl-3,4-dihydro-1H-isoquinoline-2-carboxylate | 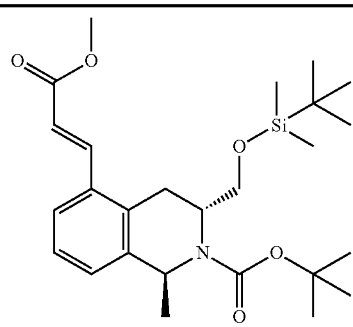 | MS (m/z): 390.2 (M-BOC + 1). |

Preparation 16

Synthesis of tert-butyl (1S,3R)-3-[[tert-butyl(dimethyl)silyl]oxymethyl]-5-(3-ethoxy-3-oxo-propyl)-1-methyl-3,4-dihydro-1H-isoquinoline-2-carboxylate

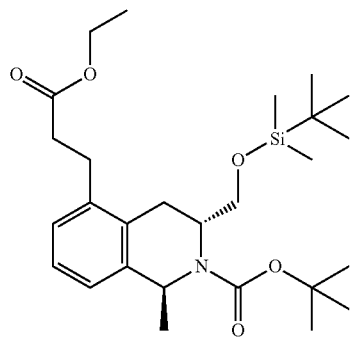 [SMILES: CCOC(=O)CCc1cccc2c1C[C@H](CO[Si](C)(C)C(C)(C)C)N(C(=O)OC(C)(C)C)[C@H]2C]

acetyl]-1-methyl-1,2,3,4-tetrahydroisoquinolin-5-yl}propanoate

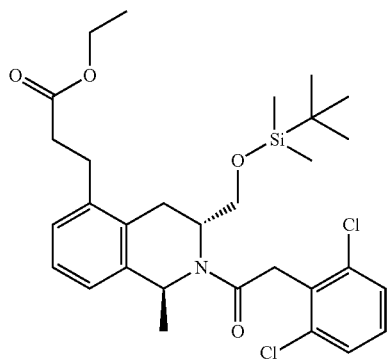 [SMILES: CCOC(=O)CCc1cccc2c1C[C@H](CO[Si](C)(C)C(C)(C)C)N(C(=O)Cc1c(Cl)cccc1Cl)[C@H]2C]

In the dry box to a 85 ml Parr autoclave with stir bar and glass liner, add 1,1'-bis(di-i-propylphosphino)ferrocene(1,5-cyclooctadiene)rhodium(I) tetrafluoroborate (7 mg, 0.010 mmol). Add ethyl (2E)-3-{(1S,3R)-3-({[tert-butyl(dimethyl)silyl]oxy}methyl)-2-[(2,6-dichlorophenyl)acetyl]-1-methyl- 1,2,3,4-tetrahydroisoquinolin-5-yl}prop-2-enoate (133 mg, 0.23 mmol) as a solution in anhydrous methanol (5 mL). Seal the autoclave and remove from the dry box. Purge the vessel with hydrogen and pressurize to 690 kPa of hydrogen. Stir at room temperature overnight. Vent and open the vessel. Concentrate the reaction mixture under reduced pressure. Purify the residue by silica gel chromatography, eluting with 25% methyl t-butyl ether:hexanes to give the title compound as a clear colorless oil (121 mg, 0.21 mmol). MS (m/z): 578 (M+1).

Preparation 18

Synthesis of (1S,3R)-5-bromo-3-({[tert-butyl(dimethyl)silyl]oxy}methyl)-1-methyl-1,2,3,4-tetrahydroisoquinoline hydrochloride

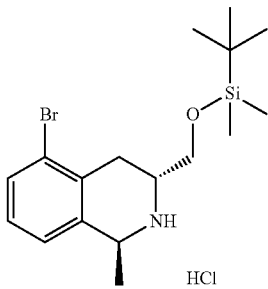 [SMILES: C[C@@H]1N[C@@H](CO[Si](C)(C)C(C)(C)C)Cc2c(Br)cccc21 ; Cl]

Add hydrogen chloride (267.24 g, 1.02 mol, 4M in 1,4-dioxane) to (1S,3R)-5-bromo-3-({[tert-butyl(dimethyl)silyl]oxy}methyl)-1-methyl-1,2,3,4-tetrahydroisoquinoline (419 g, 1.02 mol) in isopropyl acetate (4.19 L) at 10° C. and stir for 15 minutes in an appropriate vessel. Filter the mixture and wash the filter cake with isopropyl acetate (2.5 L), dry on the filter for 30 minutes, then under vacuum in an oven at 40° C. for 16 hours to give the title compound (380 g, 0.89 mol). MS (m/z): 370(M-Cl ($^{79}$Br)), 372(M-Cl ($^{81}$Br)).

Preparation 19

Synthesis of (E)-4-[(1S,3R)-3-[[tert-butyl(dimethyl)silyl]oxymethyl]-1-methyl-1,2,3,4-tetrahydroisoquinolin-5-yl]-2-methyl-but-3-en-2-ol

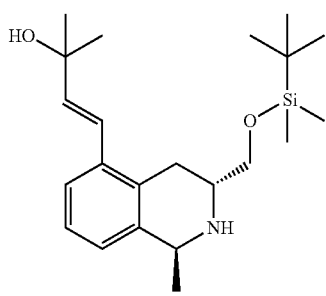 [SMILES: C[C@@H]1N[C@@H](CO[Si](C)(C)C(C)(C)C)Cc2c(/C=C/C(C)(C)O)cccc21]

Add (1S,3R)-5-bromo-3-({[tert-butyl(dimethyl)silyl]oxy}methyl)-1-methyl-1,2,3,4-tetrahydroisoquinoline hydrochloride (310 g, 723.83 mmol) and 2-methylbut-3-en-2-ol (508.95 g, 5.79 mol) to N,N-dimethylformamide (1.08 L) in an appropriate vessel and degas by bubbling nitrogen through the solution for 10 minutes. Add potassium carbonate (315.12 g, 2.28 mol), 2-dicyclohexylphosphino-2',6'-dimethoxybiphenyl (15.32 g, 36.19 mmol) and palladium (II) acetate (8.29 g, 36.19 mmol) and degas by bubbling nitrogen through the mixture for 15 minutes then heat to 125° C. After 16 hours, cool the mixture to 20° C. and dilute with ethyl acetate (1.5 L) and water (2.5 L). Wash the ethyl acetate layer with brine (2.5 L), then dry over sodium sulfate and concentrate under reduced pressure to give a residue. Purify the residue by flash chromatography, eluting with 0-50% ethyl acetate in isohexanes to give the title compound (193 g, 459.1 mmol). MS (m/z): 376(M+1).

Preparation 20

Synthesis of 4-[(1S,3R)-3-[[tert-butyl(dimethyl)silyl]oxymethyl]-1-methyl-1,2,3,4-tetrahydroisoquinolin-5-yl]-2-methyl-butan-2-ol

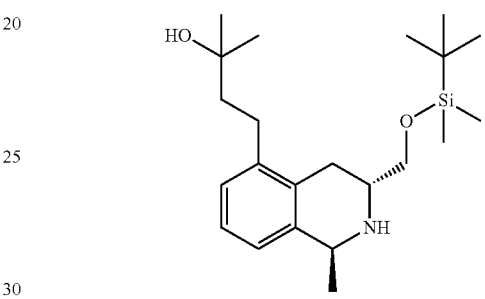

Add a solution of (E)-4-[(1S,3R)-3-[[tert-butyl(dimethyl)silyl]oxymethyl]-1-methyl-1,2,3,4-tetrahydroisoquinolin-5-yl]-2-methyl-but-3-en-2-ol (68 g, 168.83 mmol) in ethanol (816 mL) to a pressure hydrogenation vessel and add 5% palladium on activated carbon (35.83 g, 16.84 mmol). Purge the vessel with hydrogen gas, pressurise to 470 kPa of hydrogen gas and stir at 25° C. After 16 hours, vent the vessel and filter the reaction mixture through diatomaceous earth. Wash the diatomaceous earth with ethyl acetate and concentrate the filtrate under reduced pressure to give an oil. Dissolve the oil in ethyl acetate (1 L) and concentrate under reduced pressure to give the title compound (64 g, 161 mmol). MS (m/z): 378.2 (M+1).

Preparation 21

Synthesis of 1-[(1S,3R)-3-({[tert-butyl(dimethyl)silyl]oxy}methyl)-5-(3-hydroxy-3-methylbutyl)-1-methyl-3,4-dihydroisoquinolin-2(1H)-yl]-2-(2,6-dichlorophenyl)ethanone

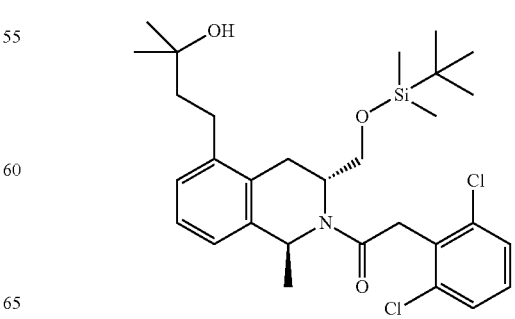

Dissolve 4-[(1S,3R)-3-[[tert-butyl(dimethyl)silyl]oxymethyl]-1-methyl-1,2,3,4-tetrahydroisoquinolin-5-yl]-2-methyl-butan-2-ol (0.21 g, 0.36 mmol) in THF (2.0 mL). Cool on a dry ice-acetone bath. Add methyl lithium (0.67 mL, 1.07 mmol, 1.6 M in diethyl ether) slowly and stir on the dry ice-acetone bath for 4 hours. Add saturated ammonium chloride solution (2 mL). Remove the dry ice-acetone bath and allow the mixture to warm to room temperature. Extract with ethyl acetate. Combine the ethyl acetate extracts; wash with brine, dry over sodium sulfate, filter, and concentrate under reduced pressure to give clear colorless oil. Purify the residue by silica gel chromatography, eluting with ethyl acetate: hexanes (gradient, 0-30%) to give the title compound as clear, colorless oil (0.16 g, 0.29 mmol). MS (m/z): 564 (M+1).

Alternative synthesis of 1-[(1S,3R)-3-({[tert-butyl (dimethyl)silyl]oxy}methyl)-5-(3-hydroxy-3-methyl-butyl)-1-methyl-3,4-dihydroisoquinolin-2(1H)-yl]-2-(2,6-dichlorophenyl)ethanone Add 1,1'-carbonyldiimidazole (112.9 g, 682.36 mmol) to a mixture of 2,6-dichlorophenylacetic acid (173.09 g, 818.83 mmol) in tetrahydrofuran (1.63 L) in an appropriate vessel and stir at 25° C. After 1 hour add a solution of 4-[(1S,3R)-3-[[tert-butyl(dimethyl)silyl]oxymethyl]-1-methyl-1,2,3,4-tetrahydroisoquinolin-5-yl]-2-methyl-butan-2-ol (217 g, 545.89 mmol) in tetrahydrofuran (1.63 L) to the mixture, heat the mixture to 45° C. and stir. After 24 hours, cool the mixture to 20° C., remove 2 L of tetrahydrofuran by concentrating under reduced pressure and dilute the residues with ethyl acetate (2.5 L). Wash the ethyl acetate solution with saturated aqueous ammonium chloride (1.5 L), 1M aqueous sodium hydroxide (1 L), water (1 L) and brine (1.5 L). Dry the organics over anhydrous sodium sulfate and concentrate under reduced pressure to give the title compound (376 g, 532.70 mmol). MS (m/z): 564.2 (M+1 ($^{35}$Cl)), 566.2 (M+1 ($^{37}$Cl)).

The following compound is prepared essentially by the method of Preparation 21.

EXAMPLE 1

Synthesis of 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone

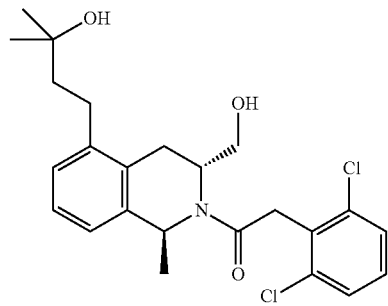 [SMILES: C[C@H]1c2cccc(CCC(C)(C)O)c2C[C@H](CO)N1C(=O)Cc1c(Cl)cccc1Cl]

Dissolve 1-[(1S,3R)-3-({[tert-butyl(dimethyl)silyl]oxy}methyl)-5-(3-hydroxy-3-methylbutyl)-1-methyl-3,4-dihydroisoquinolin-2(1H)-yl]-2-(2,6-dichlorophenyl)ethanone (0.16 g, 0.28 mmol) in THF (2.8 mL). Add tetrabutylammonium fluoride (0.30 mL, 0.30 mmol, 1M in THF). Stir 40 min. Add saturated ammonium chloride solution and extract with ethyl acetate. Combine the ethyl acetate extracts; wash with water and brine, dry over sodium sulfate, filter, and concentrate under reduced pressure to give a residue. Purify the residue by silica gel chromatography, eluting with ethyl acetate: hexanes (gradient, 0-60%) to give the title compound as a white foam (0.12 g, 0.26 mmol). MS (m/z): 450 (M+1).

Alternative synthesis of 2-(2,6-dichlorophenyl)-1-[(1S,3R)-3-(hydroxymethyl)-5-(3-hydroxy-3-methyl-butyl)-1-methyl-3,4-dihydroisoquinolin-2(1H)-yl] ethanone Add tetra-n-butylammonium fluoride (651.71 mL, 651.71 mmol, 1M in THF) to a solution of 1-[(1S,3R)-3-[[tert-butyl (dimethyl)silyl]oxymethyl]-5-(3-hydroxy-3-methyl-butyl)-1-methyl-3,4-dihydroisoquinolin-2(1H)-yl]-2-(2,6-dichlorophenyl)ethanone (400 g, 566.71 mmol) in tetrahydrofuran (4 L) at 5° C. in an appropriate vessel. Heat the mixture to 20° C. and stir. After 3 hours, remove 3 L of tetrahydrofuran by concentrating under reduced pressure and dilute the residues with ethyl acetate (2.5 L). Wash the organics with saturated aqueous ammonium chloride (2 L), water (2 L) and brine (2×2 L). Dry the ethyl acetate solution over anhydrous sodium sulfate and concentrate under reduced pressure to give an oil. Dissolve this oil in 2-propanol (2.5 L) and concentrate under

| Prep. No. | Chemical name | Structure | Physical data |
|---|---|---|---|
| 22 | tert-butyl (1S,3R)-3-[[tert-butyl(dimethyl)silyl]oxymethy]-5-(3-hydroxy-3-methyl-butyl)-1-methyl-3,4-dihydro-1H-isoquinoline-2-carboxylate | | MS (m/z): 478.2 (M + 1). | reduced pressure to give an oil. Purify by chiral SFC using AS-H column (50×250 mm, 5 micron particle size) eluting with 80% supercritical carbon dioxide and 20% of a 0.2% solution of diethylmethylamine in isopropyl alcohol at 280 g/min to give the title compound (182.8 g, 389.62 mmol). MS (m/z): 450.2 (M+1 ($^{35}$Cl)), 452.2 (M+1 ($^{37}$Cl)). Optical rotation: $[\alpha]^{20}_D$ −39.4° (c=0.95, MeOH).

EXAMPLE 2

Cocrystallization of 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid

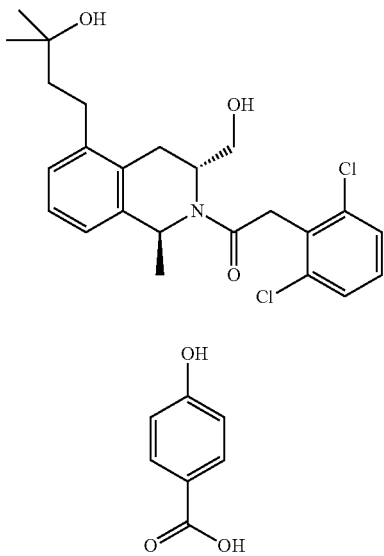

Compounds 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone (402.56 mg) and 4-hydroxybenzoic acid (144.7 mg) are placed in a 40 mL vial along with a stirbar. The vial is filled to the brim with water (39 mL). The sample is stirred at 1200 rpm at 50° C. (stirplate setting). Silicon oil is dripped around the base of the vial to ensure good thermal transfer with the hotplate. A thick white slurry results with chunks of off-white solid. After an hour of slurrying, a thermometer inserted through the septum of the vial read 40.5° C., and the sample had turned into homogenous slurry of bright white solid. After overnight slurry, the sample is homogenous slurry of flocculent white solid. The thermometer reads 43.1° C. Polarized light microscopy shows full birefringence. The bright white solid is isolated by vacuum filtration and dried in place under air stream for 10 minutes. The sample is placed in the 75° C. vacuum oven for two hours to provide the title composition as a white crystalline solid (484 mg, 94.9% yield).

Melting point onset=160.0° C. (differential scanning calorimetry).

X-Ray Powder Diffraction

The X-ray diffraction (XRD) patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology or habit. Where the effects of preferred orientation are present, peak intensities are altered, but the characteristic peak positions of the polymorph are unchanged. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of 0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. (United States Pharmacopeia #35, National Formulary #30, Chapter <941>, pages 427-432, 2012). The crystal form diffraction patterns, collected at ambient temperature and relative humidity, are adjusted based on NBS standard reference material 675 (mica) with peaks at 8.853 and 26.774 degrees 2-theta.

A prepared sample of the co-crystal of Example 2 is characterized by an X-ray diffraction pattern using CuKa radiation as having diffraction peaks (2-theta values) as described in Table 3 below, and in particular having peaks at 18.2 in combination with one or more of the peaks selected from the group consisting of 16.0, 25.4, and 7.0; with a tolerance for the diffraction angles of 0.2 degrees.

TABLE 3

| | Example 2 | |
|---|---|---|
| Peak | Angle (°2-Theta) +/−0.2° | Relative Intensity (% of most intense peak) |
| 1 | 7.0 | 74.00 |
| 2 | 15.0 | 53.70 |
| 3 | 16.0 | 87.60 |
| 4 | 17.4 | 66.20 |
| 5 | 18.2 | 100.00 |
| 6 | 19.7 | 63.00 |
| 7 | 20.2 | 54.80 |
| 8 | 21.0 | 63.60 |
| 9 | 23.4 | 29.40 |
| 10 | 25.4 | 74.20 |

Alternative preparation of cocrystal of 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid To a 20 mL vial is added 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone (2.00 g, 1.00 equiv; 4.44 mmoles). Acetone (4 mL) is added while stirring at room temperature. A clear solution is formed. 4-Hydroxybenzoic acid (0.756 g; 1.23 equiv; 5.47 mmoles) is added while stirring at room temperature. A slight suspension is formed then a thick suspension. The mixture is heated on hot plate to 60° C. Acetone in 1 mL aliquots is added until a nice mixing suspension is observed at 60° C. Total acetone added is 9.00 mL (122.43 mmoles, 7.11 g). The temperature is held at ~60° C. for several hours. The mixture is cooled to room temperature and placed in refrigerator to improve recovery. The resulting solid is collected by vacuum filtration, rinsed with 2 mL of acetone and dried in a vacuum oven overnight at 40° C. to provide the title composition as a white crystalline solid. HPLC analysis demonstrates the molar ratio of 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone to 4-hydroxybenzoic acid in the cocrystal is one to one.

HPLC Analysis

Column: Agilent ZORBAX Bonus-RP, Rapid Resolution, 4.6×75 mm, 3.5μ
Column temperature: 30° C.
Injection volume: 2 μL
Detection: UV
   2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone (Example 1) @ 219 nm
   4-hydroxybenzoic acid @ 256 nm
Flow rate: 1.5 mL/min
Mobile phase: A) 0.1% TFA in water
   B) 0.1% TFA in acetonitrile

| Gradient Table | | |
| --- | --- | --- |
| Time, minutes | % A | % B |
| 0 | 95 | 5 |
| 9.5 | 23 | 77 |
| 12.1 | 23 | 77 |
| 13.0 | 5 | 95 |
| 16.0 | 5 | 95 |
| 16.1 | 95 | 5 |
| 20.0 | 95 | 5 |

| Relative Ratio | | | |
| --- | --- | --- | --- |
| Compound | Molecular Weight | Theoretical Potency for 1 to 1 | Assayed Potency (n = 3) |
| Example 1 | 450.4 | 76.5% | 81.06% ± 0.15% |
| 4-hydroxy-benzoic acid | 138.1 | 23.5% | 23.74% ± 0.20% |

Second alternative preparation of cocrystal of 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid Compounds 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone (45.06 g, 0.1 mol) and 4-hydroxybenzoic acid (14.5 g, 1.05 mol eq) are slurried at 23° C. in 53:47 isopropyl alcohol:heptane (236 mL, 4 volumes) and heated to 65° C. The resulting solution is seeded with cocystals of 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid (553 mg, 1.0 wt. % seed load) and stirred at 65° C. for 30 minutes. Heptane (943 mL, 16 volumes³) is added at 65° C. over 4.6 hours. The slurry is stirred at 65° C. for a further 30 minutes, cooled to 23° C. over 2 hours, stirred overnight at 23° C., and vacuum filtered. The product solids are rinsed with 10:90 isopropyl alcohol:heptane (2×50 mL) and heptane (50 mL) then dried in a vacuum oven at 40° C. for 2 hours to yield the title composition as a white crystalline product (51.3 g, 86.3 wt % yield). Melting point onset=162.2° C. (differential scanning calorimetry).

Preparation 23

Synthesis of 4-[(1S,3R)-3-(hydroxymethyl)-1-methyl-1,2,3,4-tetrahydroisoquinolin-5-yl]-2-methyl-butan-2-ol hydrochloride

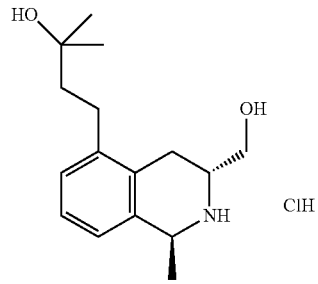 [SMILES: C[C@@H]1N[C@@H](CO)Cc2c(CCC(C)(C)O)cccc21 ; Cl]

Dissolve tert-butyl (1S,3R)-3-[[tert-butyl(dimethyl)silyl]oxymethyl]-5-(3-hydroxy-3-methyl-butyl)-1-methyl-3,4-dihydro-1H-isoquinoline-2-carboxylate (161 mg, 0.34 mmol) in ethyl acetate (962 μL). Cool on an ice bath. Add hydrogen chloride (843 μL, 3.37 mmol, 4M in dioxane) and stir on the ice bath for 4 hours. Concentrate under reduced pressure. Dissolve in ethanol and concentrate under reduced pressure to give the title compound (100 mg, 0.34 mmol). MS (m/z): 264.2 (M+1).

The following compound is prepared essentially by the method of Preparation 23.

| Prep. No. | Chemical name | Structure | Physical data |
| --- | --- | --- | --- |
| 24 | 4-[(1S,3R)-3-(hydroxymethyl)-1-methyl-1,2,3,4-tetra-hydroisoquinolin-5-yl]-2-methyl-butan-2-ol | 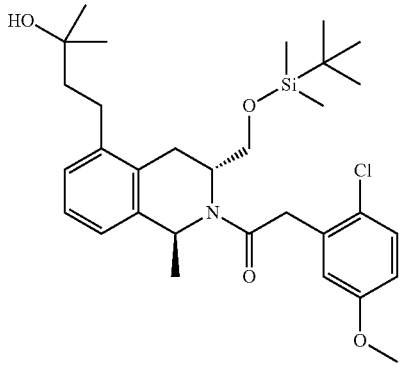 | MS (m/z): 264.2 (M + 1). |

Preparation 25

Synthesis of 1-[(1S,3R)-3-[[tert-butyl(dimethyl)silyl]oxymethyl]-5-(3-hydroxy-3-methyl-butyl)-1-methyl-3,4-dihydro-1H-isoquinolin-2-yl]-2-(2-chloro-5-methoxy-phenyl)ethanone Dissolve 4-[(1S,3R)-3-[[tert-butyl(dimethyl)silyl]oxymethyl]-1-methyl-1,2,3,4-tetrahydroisoquinolin-5-yl]-2-methyl-butan-2-ol (0.36 g, 0.95 mol) in dichloromethane (9.5 mL). Add diisopropylethylamine (499 µL, 2.86 mmol). Add 2-(2-chloro-5-methoxy-phenyl)acetic acid (229.5 mg, 1.14 mmol). Add O-(7-aza-1H-benzotriazol-1-yl)-N,N,N',N'-tetramethyluronium hexafluorophosphate (561 mg, 1.40 mmol) and stir at ambient temperature overnight. Dilute the reaction mixture with dichloromethane and wash with water and brine, dry over sodium sulfate, filter, and concentrate under reduced pressure to give a brown oil. Purify the residue by silica gel chromatography, eluting with acetone: hexanes (gradient, 0-20%) to give the title compound as an opaque oil (0.46 g, 0.82 mmol). MS (m/z): 560.2 (M+1).

The following compounds are prepared essentially by the method of Preparation 25.

Dissolve 1-[(1S,3R)-5-bromo-3-({[tert-butyl(dimethyl)silyl]oxy}methyl)-1-methyl-3,4-dihydroisoquinolin-2(1H)-yl]-2-(2,6-dichlorophenyl)ethanone (300 mg, 0.54 mmol) and vinylboronic acid dibutyl ester (0.24 mL, 1.08 mmol) in 1,4-dioxane (5.4 mL). Add aqueous Na$_2$CO$_3$ solution (2.7 mL, 2M in water). Degas with nitrogen 10 min Add bis(triphenylphosphine)palladium(II) chloride (76 mg, 0.11 mmol). Heat to 80° C. Stir 2 hours. Add water and extract with ethyl acetate three times. Combine the ethyl acetate extracts, dry over sodium sulfate, filter, and concentrate under reduced pressure to give a residue. Purify the residue by silica gel chromatography, eluting with ethyl acetate:hexanes (gradient, 5-80%) to give the title compound as a white foam (220 mg, 0.44 mmol). MS (m/z): 504 (M+1).

Preparation 29

Synthesis of 1-((1S,3R)-3-(((tert-butyldimethylsilyl)oxy)methyl)-5-(1-hydroxyethyl)-1-methyl-3,4-dihy-

| Prep. No. | Chemical name | Structure | Physical data |
|---|---|---|---|
| 26 | 1-[(1S,3R)-3-[[tert-butyl(dimethyl)silyl]oxymethyl]-5-(3-hydroxy-3-methyl-butyl)-1-methyl-3,4-dihydro-1H-isoquinolin-2-yl]-2-(6-chloro-2-fluoro-3-methoxy-phenyl)ethanone | 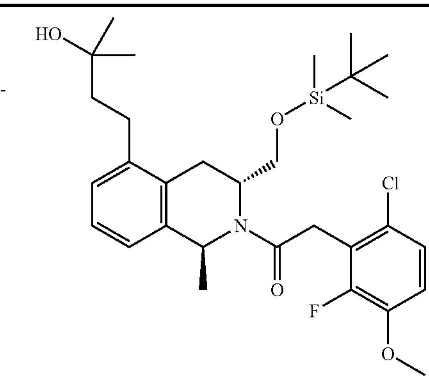 | MS (m/z): 577.8 (M + 1). |
| 27 | 1-[(1S,3R)-3-[[tert-butyl(dimethyl)silyl]oxymethyl]-5-(3-hydroxy-3-methyl-butyl)-1-methyl-3,4-dihydro-1H-isoquinolin-2-yl]-2-(2-chloro-6-methoxy-phenyl)ethanone | 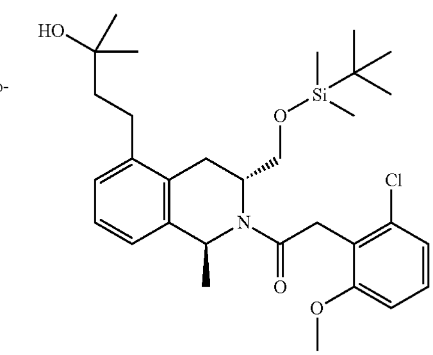 | MS (m/z): 560.2 (M + 1). |

Preparation 28

Synthesis of 1-((1S,3R)-3-(((tert-butyldimethylsilyl)oxy)methyl)-1-methyl-5-vinyl-3,4-dihydroisoquinolin-2(1H)-yl)-2-(2,6-dichlorophenyl)ethan-1-one droisoquinolin-2(1H)-yl)-2-(2,6-dichlorophenyl)ethan-1-one (mixture of diastereomers) and 1-((1S,3R)-3-(((tert-butyldimethylsilyl)oxy)methyl)-5-(2-hydroxyethyl)-1-methyl-3,4-dihydroisoquinolin-2(1H)-yl)-2-(2,6-dichlorophenyl)ethan-1-one

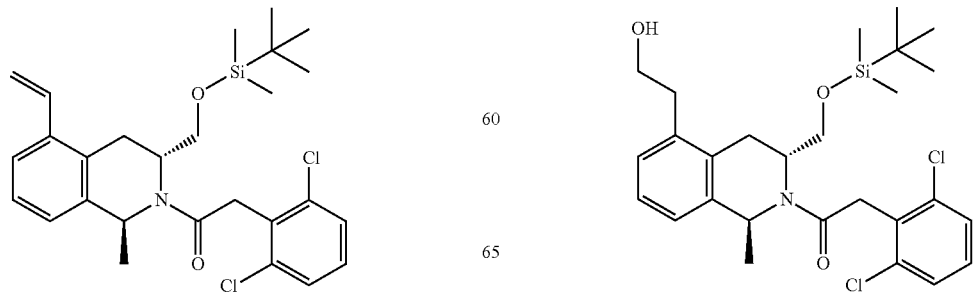

and

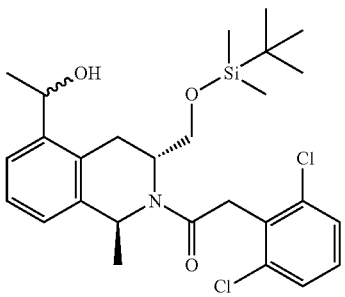 [SMILES: CC(O)c1cccc2c1C[C@H](CO[Si](C)(C)C(C)(C)C)N(C(=O)Cc1c(Cl)cccc1Cl)[C@H]2C]

Dissolve 1-((1S,3R)-3-(((tert-butyldimethylsilyl)oxy)methyl)-1-methyl-5-vinyl-3,4-dihydroisoquinolin-2(1H)-yl)-2-(2,6-dichlorophenyl)ethan-1-one (477 mg, 0.95 mmol) in THF (9.5 mL). Cool to 0° C. Add BH$_3$ (1.9 mL, 1.89 mmol, 1M in THF). Stir 4 h at room temperature. Cool to 0° C. Add NaOH (3.8 mL, 3 M in water) and H$_2$O$_2$ (0.58 mL, 30% wt/wt % in water). Stir overnight at room temperature. Add ethyl acetate, wash with saturated NaHCO$_3$ solution and brine, dry over sodium sulfate, filter, and concentrate under reduced pressure to give a residue. Purify the residue by silica gel chromatography, eluting with ethyl acetate: hexanes (gradient, 5-60%) to give 1-((1S,3R)-3-(((tert-butyldimethylsilyl)oxy)methyl)-5-(1-hydroxyethyl)-1-methyl-3,4-dihydroisoquinolin-2(1H)-yl)-2-(2,6-dichlorophenyl)ethan-1-one (mixture of diastereomers) as a white foam (92 mg, 0.19 mmol). MS (m/z): 522 (M+1); and 1-((1S,3R)-3-(((tert-butyldimethylsilyl)oxy)methyl)-5-(2-hydroxyethyl)-1-methyl-3,4-dihydroisoquinolin-2(1H)-yl)-2-(2,6-dichlorophenyl)ethan-1-one as a white foam (254 mg, 0.49 mmol). MS (m/z): 522 (M+1).

Preparation 30

Synthesis of 1-((1S,3R)-5-acetyl-3-(((tert-butyldimethylsilyl)oxy)methyl)-1-methyl-3,4-dihydroisoquinolin-2(1H)-yl)-2-(2,6-dichlorophenyl)ethan-1-one

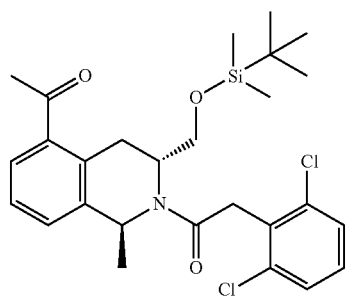 [SMILES: CC(=O)c1cccc2c1C[C@H](CO[Si](C)(C)C(C)(C)C)N(C(=O)Cc1c(Cl)cccc1Cl)[C@H]2C]

Dissolve 1-((1S,3R)-3-(((tert-butyldimethylsilyl)oxy)methyl)-5-(1-hydroxyethyl)-1-methyl-3,4-dihydroisoquinolin-2(1H)-yl)-2-(2,6-dichlorophenyl)ethan-1-one (92 mg, 176 μmol, mixture of two diastereomers) in CH$_2$Cl$_2$ (1.8 mL). Add NaHCO$_3$ (92 mg, 1.1 mmol) and 3,3,3-Triacetoxy-3-iodophthalide (90 mg, 211 μmol) at room temperature. Stir 40 min. Add saturated NaHCO$_3$ solution and saturated Na$_2$S$_2$O$_3$ solution, extract with ethyl acetate three times. Combine the ethyl acetate extracts, dry over sodium sulfate, filter, and concentrate under reduced pressure to give a residue. Purify the residue by silica gel chromatography, eluting with ethyl acetate: hexanes (gradient, 5-60%) to give the title compound as a white foam (0.068 g, 130 μmol). MS (m/z): 522 (M+1). The following compounds are prepared essentially by the method of Preparation 30.

| Prep. No. | Name | Structure | Physical Data |
|---|---|---|---|
| 31 | 1-((1S,3R)-3-(((tert-butyldimethylsilyl)oxy)methyl)-2-(2-(2,6-dichlorophenyl)acetyl)-1-methyl-1,2,3,4-tetrahydroisoquinolin-5-yl)propan-2-one | 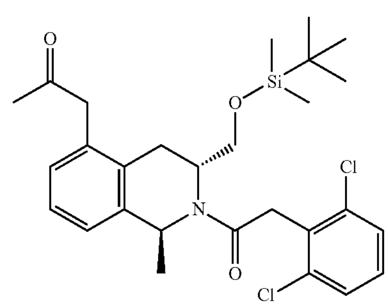 [SMILES: CC(=O)Cc1cccc2c1C[C@H](CO[Si](C)(C)C(C)(C)C)N(C(=O)Cc1c(Cl)cccc1Cl)[C@H]2C] | MS (m/z): 534.2 (M + 1). |
| 32 | 1-((1S,3R)-3-(((tert-butyldimethylsilyl)oxy)methyl)-2-(2-(2-chloro-6-fluorophenyl)acetyl)-1-methyl-1,2,3,4-tetrahydroisoquinolin-5-yl)propan-2-one | 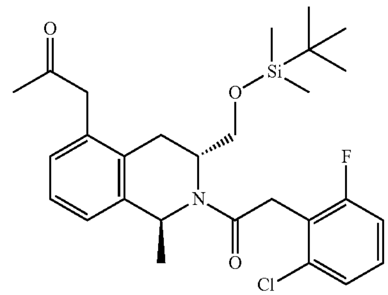 [SMILES: CC(=O)Cc1cccc2c1C[C@H](CO[Si](C)(C)C(C)(C)C)N(C(=O)Cc1c(F)cccc1Cl)[C@H]2C] | MS (m/z): 518.2 (M + 1). |

Preparation 33

Synthesis of 2-((1S,3R)-3-(((tert-butyldimethylsilyl)oxy)methyl)-2-(2-(2,6-dichlorophenyl)acetyl)-1-methyl-1,2,3,4-tetrahydroisoquinolin-5-yl)acetaldehyde

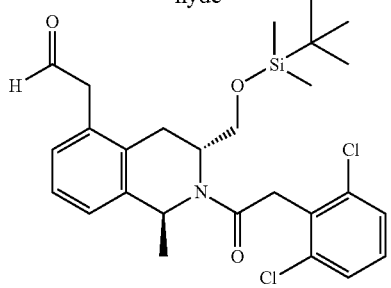 [SMILES: C[C@H]1c2cccc(CC=O)c2C[C@H](CO[Si](C)(C)C(C)(C)C)N1C(=O)Cc1c(Cl)cccc1Cl]

Dissolve 1-((1S,3R)-3-(((tert-butyldimethylsilyl)oxy)methyl)-5-(2-hydroxyethyl)-1-methyl-3,4-dihydroisoquinolin-2(1H)-yl)-2-(2,6-dichlorophenyl)ethan-1-one (160 mg, 0.31 mmol) in CH$_2$Cl$_2$ (3.1 mL). Add NaHCO$_3$ (160 mg, 1.90 mmol) and 3,3,3-Triacetoxy-3-iodophthalide (156 mg, 0.37 mmol) at room temperature. Stir 40 min. Add saturated NaHCO$_3$ solution and saturated Na$_2$S$_2$O$_3$ solution, extract with ethyl acetate three times. Combine the ethyl acetate extracts, dry over sodium sulfate, filter, and concentrate under reduced pressure to give a residue. Purify the residue by silica gel chromatography, eluting with ethyl acetate: hexanes (gradient, 5-60%) to give the title compound as a white foam (140 mg, 0.27 mmol). MS (m/z): 520.2 (M+1).

Preparation 34

Synthesis of 1-((1S,3R)-3-(((tert-butyldimethylsilyl)oxy)methyl)-5-(2-hydroxypropyl)-1-methyl-3,4-dihydroisoquinolin-2(1H)-yl)-2-(2,6-dichlorophenyl)ethan-1-one (mixture of two diastereomers)

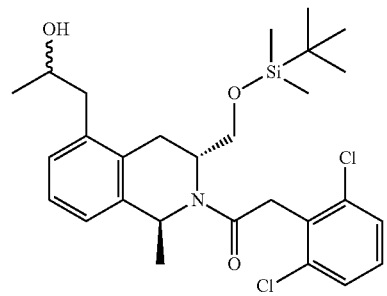 [SMILES: CC(O)Cc1cccc2c1C[C@H](CO[Si](C)(C)C(C)(C)C)N(C(=O)Cc1c(F)cccc1Cl)[C@H]2C]

Dissolve 2-((1S,3R)-3-(((tert-butyldimethylsilyl)oxy)methyl)-2-(2-(2,6-dichlorophenyl)acetyl)-1-methyl-1,2,3,4-tetrahydroisoquinolin-5-yl)acetaldehyde (138 mg, 0.27 mmol) in THF (2.7 mL). Cool to 0° C., add MeMgCl (0.097 mL, 0.29 mmol, 3M in Et$_2$O). Stir 30 min at 0° C. Add water and extract with ethyl acetate three times. Combine the ethyl acetate extracts, dry over sodium sulfate, filter, and concentrate under reduced pressure to give a residue. Purify the residue by silica gel chromatography, eluting with ethyl acetate: hexanes (gradient, 2-60%) to give the title compound as a white foam (122 mg, 0.23 mmol). MS (m/z): 536.2 (M+1).

The following compound is prepared essentially by the method of Preparation 34.

| Prep. No. | Name | Structure | Physical Data |
|---|---|---|---|
| 35 | 1-((1S,3R)-3-(((tert-butyldimethylsilyl)oxy)methyl)-5-(2-hydroxypropyl)-1-methyl-3,4-dihydroisoquinolin-2(1H)-yl)-2-(2-chloro-6-fluorophenyl)ethan-1-one (mixture of two diastereomers) | 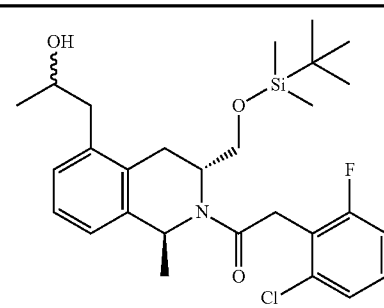 | MS (m/z): 520.2 (M + 1). |

Preparation 36

Synthesis of 1-((1S,3R)-5-bromo-3-(((tert-butyldimethylsilyl)oxy)methyl)-1-methyl-3,4-dihydroisoquinolin-2(1H)-yl)-2-(2-chloro-6-fluorophenyl)ethan-1-one

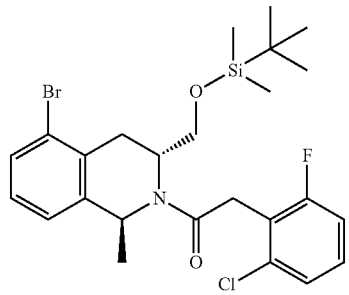 [SMILES: C[C@H]1c2cccc(Br)c2C[C@H](CO[Si](C)(C)C(C)(C)C)N1C(=O)Cc1c(F)cccc1Cl]

Dissolve (1S,3R)-5-bromo-3-(((tert-butyldimethylsilyl)oxy)methyl)-1-methyl-1,2,3,4-tetrahydroisoquinoline (1.85 g, 4.99 mmol) and 2-chloro-6-fluorophenylacetic acid (1.04 g, 5.49 mmol) in dichloromethane (50 mL). Add 0-(7-azabenzotriazol-1-yl)-N,N,N',N'-tetramethyluronium hexafluorophosphate (2.85 g, 7.49 mmol) and diisopropylethylamine (1.3 mL, 7.49 mmol) at rt. Stir 3 hours. Add water and extract with dichloromethane three times. Combine the dichloromethane extracts, dry over sodium sulfate, filter, and concentrate under reduced pressure to give a residue. Purify the residue by silica gel chromatography, eluting with ethyl acetate: hexanes (gradient, 5-60%) to give the title compound as a white foam (2.2 g, 4.07 mmol). MS (m/z): 540.2 (M+1).

Preparation 37

Synthesis of 1-((1S,3R)-3-(((tert-butyldimethylsilyl)oxy)methyl)-1-methyl-5-vinyl-3,4-dihydroisoquinolin-2(1H)-yl)-2-(2-chloro-6-fluorophenyl)ethan-1-one

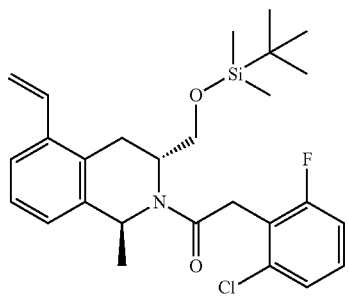 [SMILES: C=Cc1cccc2c1C[C@H](CO[Si](C)(C)C(C)(C)C)N(C(=O)Cc1c(F)cccc1Cl)[C@H]2C]

Dissolve 1-((1S,3R)-5-bromo-3-(((tert-butyldimethylsilyl)oxy)methyl)-1-methyl-3,4-dihydroisoquinolin-2(1H)-yl)-2-(2-chloro-6-fluorophenyl)ethan-1-one (1.8 g, 3.33 mmol) and vinylboronic acid dibutyl ester (1.5 mL, 6.65 mmol) in 1,4-dioxane (22 mL). Add aqueous Na₂CO₃ solution (11 mL, 2M in water). Degas with nitrogen 10 min Add bis(triphenylphosphine)palladium(II) chloride (467 mg, 0.67 mmol). Heat to 80° C. Stir 2 hours. Add water and extract with ethyl acetate three times. Combine the ethyl acetate extracts, dry over sodium sulfate, filter, and concentrate under reduced pressure to give a residue. Purify the residue by silica gel chromatography, eluting with ethyl acetate: hexanes (gradient, 5-40%) to give the title compound as a white foam (1.54 g, 3.15 mmol). MS (m/z): 488.2 (M+1).

Preparation 38

Synthesis of 1-((1S,3R)-3-(((tert-butyldimethylsilyl)oxy)methyl)-5-(2-hydroxyethyl)-1-methyl-3,4-dihydroisoquinolin-2(1H)-yl)-2-(2-chloro-6-fluorophenyl)ethan-1-one

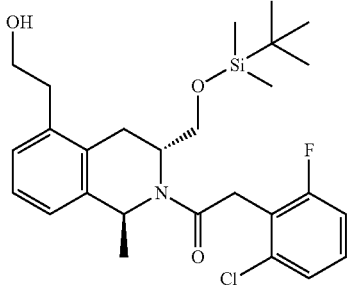

Dissolve 1-((1S,3R)-3-(((tert-butyldimethylsilyl)oxy)methyl)-1-methyl-5-vinyl-3,4-dihydroisoquinolin-2(1H)-yl)-2-(2-chloro-6-fluorophenyl)ethan-1-one (1.54 g, 3.15 mmol) in THF (31 mL). Cool to 0° C. Add BH₃ (6.3 mL, 6.3 mmol, 1M in THF). Stir 4 h at room temperature. Cool to 0° C. Add NaOH (12.6 mL, 3 M in water) and H₂O₂ (1.92 mL, 30% wt/wt % in water). Stir overnight at room temperature. Add ethyl acetate, wash with saturated NaHCO₃ solution and brine, dry over sodium sulfate, filter, and concentrate under reduced pressure to give a residue. Purify the residue by silica gel chromatography, eluting with ethyl acetate: hexanes (gradient, 5-60%) to give 1-((1S,3R)-3-(((tert-butyldimethylsilyl)oxy)methyl)-5-(2-hydroxyethyl)-1-methyl-3,4-dihydroisoquinolin-2(1H)-yl)-2-(2-chloro-6-fluorophenyl)ethan-1-one as a white foam (1.08 g, 2.13 mmol). MS (m/z): 506.2 (M+1).

Preparation 39

Synthesis of 2-((1S,3R)-3-(((tert-butyldimethylsilyl)oxy)methyl)-2-(2-(2-chloro-6-fluorophenyl)acetyl)-1-methyl-1,2,3,4-tetrahydroisoquinolin-5-yl)acetaldehyde

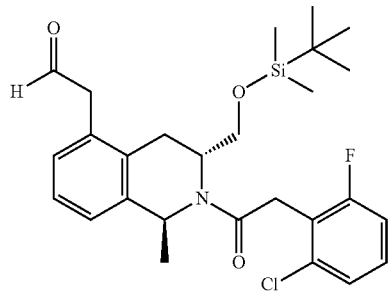 [SMILES: C[C@H]1c2cccc(CC=O)c2C[C@H](CO[Si](C)(C)C(C)(C)C)N1C(=O)Cc1c(F)cccc1Cl]

Dissolve 1-((1S,3R)-3-(((tert-butyldimethylsilyl)oxy)methyl)-5-(2-hydroxyethyl)-1-methyl-3,4-dihydroisoquinolin-2(1H)-yl)-2-(2-chloro-6-fluorophenyl)ethan-1-one (1.08 g, 2.13 mmol) in CH₂Cl₂ (21 mL). Add NaHCO₃ (1.08 g, 12.9 mmol) and 3,3,3-triacetoxy-3-iodophthalide (1.09 g, 2.56 mmol) at room temperature. Stir 40 min. Add saturated NaHCO₃ solution and saturated Na₂S₂O₃ solution, extract with ethyl acetate three times. Combine the ethyl acetate extracts, dry over sodium sulfate, filter, and concentrate under reduced pressure to give a residue. Purify the residue by silica gel chromatography, eluting with ethyl acetate: hexanes (gradient, 5-60%) to give the title compound as a white foam (0.87 g, 1.73 mmol).

Preparation 40

Synthesis of 1-((1S,3R)-3-(((tert-butyldimethylsilyl)oxy)methyl)-1-methyl-1,2,3,4-tetrahydroisoquinolin-5-yl)propan-2-one

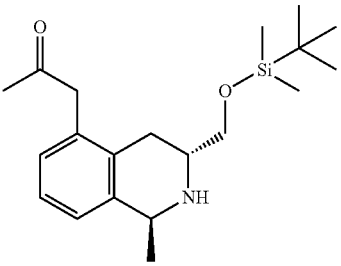 [SMILES: CC(=O)Cc1cccc2c1C[C@H](CO[Si](C)(C)C(C)(C)C)N[C@H]2C]

Mix (1S,3R)-5-bromo-3-(((tert-butyldimethylsilyl)oxy)methyl)-1-methyl-1,2,3,4-tetrahydroisoquinoline hydrochloride (2.5 g, 6.14 mmol), acetone (30 mL), potassium phosphate, Tribasic, N-hydrate (3.99 g, 18.4 mmol), CataCXium A (di(1-adamantyl)-n-butylphosphine, 220 mg, 0.61 mmol) and tris(dibenzylideneacetone)dipalladium(0) (290 mg, 0.31 mmol). Stir 2 days at 70° C. Cool to 0° C. Add water and extract with ethyl acetate three times. Combine the ethyl acetate extracts, dry over sodium sulfate, filter, and concentrate under reduced pressure to give a residue. Purify the residue by silica gel chromatography, eluting with ethyl acetate: hexanes (gradient, 10-100%) to give the title compound as a white foam (1.3 g, 3.74 mmol). MS (m/z): 348 (M+1).

Preparation 41

Synthesis of 1-((1S,3R)-3-(((tert-butyldimethylsilyl)oxy)methyl)-2-(2-(6-chloro-2-fluoro-3-methoxyphenyl)acetyl)-1-methyl-1,2,3,4-tetrahydroisoquinolin-5-yl)propan-2-one

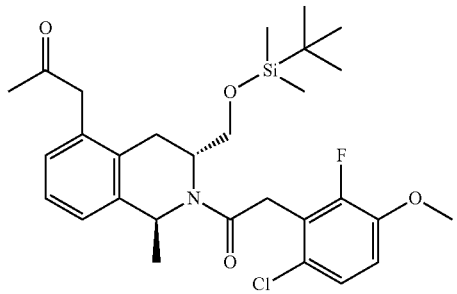 [SMILES: COc1ccc(Cl)c(CC(=O)N2[C@@H](CO[Si](C)(C)C(C)(C)C)Cc3c(CC(C)=O)cccc3[C@@H]2C)c1F]

Dissolve 1-(1S,3R)-3-(((tert-butyldimethylsilyl)oxy)methyl)-1-methyl-1,2,3,4-tetrahydroisoquinolin-5-yl)propan-2-one (1.3 g, 3.74 mmol) in dicholormethane (37 mL). Add diisopropylethylamine (2.0 mL, 11.22 mmol), 2-(6-chloro-2-fluoro-3-methoxyphenyl)acetic acid (1.06 g, 4.86 mmol), O-(7-azabenzotriazol-1-yl)-N,N,N',N'-tetramethyluronium hexafluorophosphate (1.91 g, 4.86 mmol) and at rt. Stir 16 hours. Wash with saturated aqueous NaHCO₃ solution, dry over sodium sulfate, filter, and concentrate under reduced pressure to give a residue. Purify the residue by silica gel chromatography, eluting with ethyl acetate: hexanes (gradient, 5-50%) to give the title compound as a white foam (1.6 g, 2.69 mmol). MS (m/z): 548.6 (M+1).

Preparation 42

Synthesis of 1-((1S,3R)-3-(((tert-butyldimethylsilyl)oxy)methyl)-5-(2-hydroxypropan-2-yl)-1-methyl-3,4-dihydroisoquinolin-2(1H)-yl)-2-(2,6-dichlorophenyl)ethan-1-one

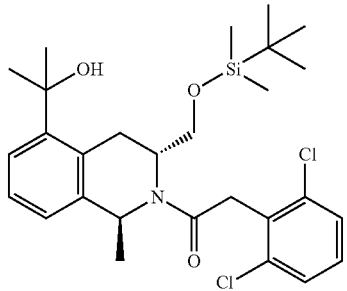 [SMILES: C[C@H]1c2cccc(C(C)(C)O)c2C[C@H](CO[Si](C)(C)C(C)(C)C)N1C(=O)Cc1c(Cl)cccc1Cl]

Dissolve 1-((1S,3R)-5-acetyl-3-(((tert-butyldimethylsilyl)oxy)methyl)-1-methyl-3,4-dihydroisoquinolin-2(1H)-yl)-2-(2,6-dichlorophenyl)ethan-1-one (68 mg, 130 μmol) in THF (1.3 mL). Cool to 0° C., add MeMgCl (87 μL, 261 μmol, 3M in Et₂O). Stir 30 min at 0° C. and 30 min at room temperature. Add MeMgCl (87 μL, 261 μmol, 3M in Et₂O) at rt. Stir 60 min. Add water and extract with ethyl acetate three times. Combine the ethyl acetate extracts, dry over sodium sulfate, filter, and concentrate under reduced pressure to give the title compound as a white foam (0.054 g, 100 μmol). MS (m/z): 536.2 (M+1).

The following compounds are prepared essentially by the method of Preparation 42.

| Prep. No. | Name | Structure | Physical Data |
|---|---|---|---|
| 43 | 1-((1S,3R)-3-(((tert-butyldimethylsilyl)oxy)methyl)-5-(2-hydroxy-2-methylpropyl)-1-methyl-3,4-dihydroisoquinolin-2(1H)-yl)-2-(2,6-dichlorophenyl)ethan-1-one | 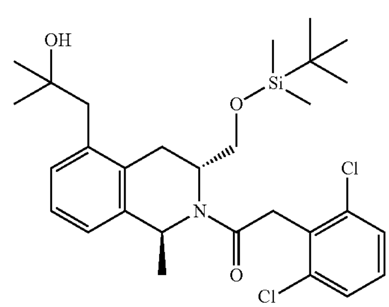 | MS (m/z): 550.2 (M + 1) |

| Prep. No. | Name | Structure | Physical Data |
|---|---|---|---|
| 44 | 1-((1S,3R)-3-(((tert-butyldimethylsilyl)oxy)methyl)-5-(2-hydroxy-2-methylpropyl)-1-methyl-3,4-dihydroisoquinolin-2(1H)-yl)-2-(2,6-dichlorophenyl)ethan-1-one | 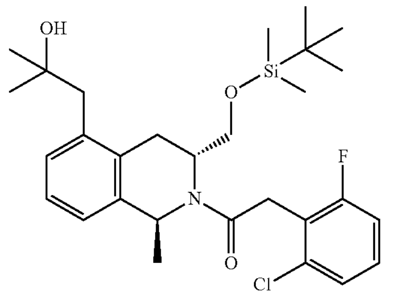 [SMILES: C[C@H]1c2cccc(CC(C)(C)O)c2C[C@H](CO[Si](C)(C)C(C)(C)C)N1C(=O)Cc1c(F)cccc1Cl] | MS (m/z): 534.2 (M + 1). |
| 45 | 1-((1S,3R)-3-(((tert-butyldimethylsilyl)oxy)methyl)-5-(2-hydroxy-2-methylpropyl)-1-methyl-3,4-dihydroisoquinolin-2(1H)-yl)-2-(6-chloro-2-fluoro-3-methoxyphenyl)ethan-1-one | 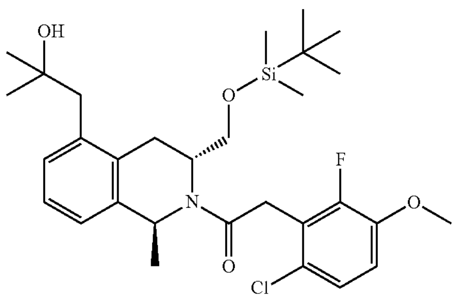 [SMILES: COc1ccc(Cl)c(CC(=O)N2[C@@H](CO[Si](C)(C)C(C)(C)C)Cc3c(CC(C)(C)O)cccc3[C@@H]2C)c1F] | MS (m/z): 564 (M + 1). |

EXAMPLE 3

Synthesis of 2-(2,6-dichlorophenyl)-1-((1S,3R)-3-(hydroxymethyl)-5-(2-hydroxypropan-2-yl)-1-methyl-3,4-dihydroisoquinolin-2(1H)-yl)ethan-1-one

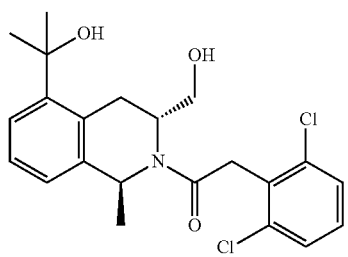 [SMILES: C[C@H]1c2cccc(C(C)(C)O)c2C[C@H](CO)N1C(=O)Cc1c(Cl)cccc1Cl]

Dissolve 1-((1S,3R)-3-(((tert-butyldimethylsilyl)oxy)methyl)-5-(2-hydroxypropan-2-yl)-1-methyl-3,4-dihydroisoquinolin-2(1H)-yl)-2-(2,6-dichlorophenyl)ethan-1-one (0.054 g, 100 μmol) in THF (1.0 mL). Add tetrabutylammonium fluoride (0.11 mL, 110 μmol, 1M in THF). Stir 30 min. Add saturated ammonium chloride solution and extract with ethyl acetate three times. Combine the ethyl acetate extracts, dry over sodium sulfate, filter, and concentrate under reduced pressure to give a residue. Purify the residue by silica gel chromatography, eluting with ethyl acetate: hexanes (gradient, 10-100%) to give the title compound as a white foam (0.03 g, 71 μmol). MS (m/z): 422 (M+1).

EXAMPLE 3a

Preparation of crystalline 2-(2,6-dichlorophenyl)-1-((1S,3R)-3-(hydroxymethyl)-5-(2-hydroxypropan-2-yl)-1-methyl-3,4-dihydroisoquinolin-2(1H)-yl)ethan-1-one Dissolve 1.932 g of 2-(2,6-dichlorophenyl)-1-((1S,3R)-3-(hydroxymethyl)-5-(2-hydroxypropan-2-yl)-1-methyl-3,4-dihydroisoquinolin-2(1H)-yl)ethan-1-one at a concentration of 128 mg/mL in cyclopentyl methyl ether while stirring at 80° C./1000 rpm. The solution begins to precipitate a white solid which is then cooled to ambient temperature after a brief slurry period. The solid is isolated by vacuum filtration and dried under nitrogen briefly before continuing in a 65° C. vacuum oven for 2 hours. 1.606 g of the title compound is recovered for a yield of 86.8%.

X-Ray Powder Diffraction

The XRD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 35-National Formulary 30 Chapter <941> Characterization of crystalline and partially crystalline solids by X-ray powder diffraction (XRPD) Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of °2θ), typically the more prominent peaks. The crystal form diffraction patterns, collected at ambient temperature and relative humidity, are adjusted based on NIST 675 standard peaks at 8.85 and 26.77 degrees 2-theta.

A prepared sample of the crystalline compound of Example 3a is characterized by an XRD pattern using CuKa radiation as having diffraction peaks (2-theta values) as described in Table 10 below. Specifically the pattern contains a peak at 14.3 in combination with one or more of the peaks selected from the group consisting of 15.7, 18.0, 18.7, 22.4 and 25.1 with a tolerance for the diffraction angles of 0.2 degrees.

TABLE 10

X-ray powder diffraction peaks of Example 3a

| Peak | Angle (2-Theta °) | Intensity (%) |
|---|---|---|
| 1 | 11.0 | 37 |
| 2 | 12.4 | 31 |
| 3 | 14.3 | 100 |
| 4 | 15.7 | 56 |
| 5 | 16.8 | 15 |
| 6 | 18.0 | 40 |
| 7 | 18.7 | 40 |
| 8 | 19.4 | 16 |
| 9 | 20.1 | 36 |
| 10 | 21.1 | 10 |
| 11 | 22.4 | 45 |
| 12 | 23.2 | 38 |
| 13 | 24.5 | 16 |
| 14 | 25.1 | 39 |
| 15 | 26.1 | 11 |
| 16 | 28.3 | 26 |

The following compounds are prepared essentially by the method of Example 3.

| Example No. | Name | Structure | Physical Data |
|---|---|---|---|
| 4 | 2-(2,6-dichlorophenyl)-1-((1S,3R)-5-(2-hydroxy-2-methylpropyl)-3-(hydroxymethyl)-1-methyl-3,4-dihydroisoquinolin-2(1H)-yl)ethan-1-one | 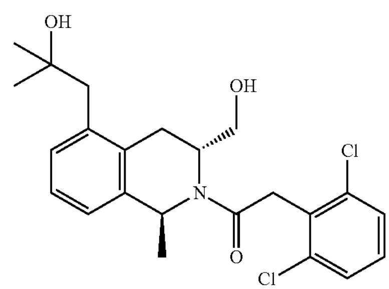 [SMILES: C[C@H]1c2cccc(CC(C)(C)O)c2C[C@H](CO)N1C(=O)Cc1c(Cl)cccc1Cl] | MS (m/z): 436 (M + 1) |
| 5 | 2-(2-chloro-6-fluorophenyl)-1-((1S,3R)-5-(2-hydroxy-2-methylpropyl)-3-(hydroxymethyl)-1-methyl-3,4-dihydroisoquinolin-2(1H)-yl)ethan-1-one | 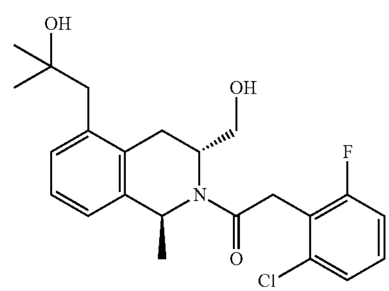 [SMILES: C[C@H]1c2cccc(CC(C)(C)O)c2C[C@H](CO)N1C(=O)Cc1c(F)cccc1Cl] | MS (m/z): 420.2 (M + 1) |
| 6 | 2-(6-chloro-2-fluoro-3-methoxyphenyl)-1-((1S,3R)-5-(2-hydroxy-2-methylpropyl)-3-(hydroxymethyl)-1-methyl-3,4-dihydroisoquinolin-2(1H)-yl)ethan-1-one | 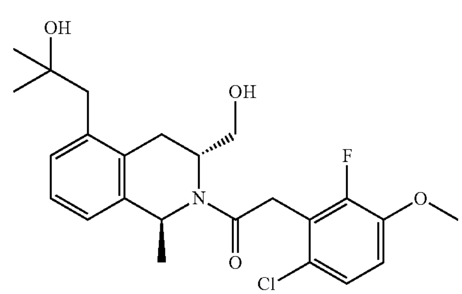 [SMILES: COc1ccc(Cl)c(CC(=O)N2[C@@H](CO)Cc3c(CC(C)(C)O)cccc3[C@@H]2C)c1F] | MS (m/z): 449.8 (M + 1). |

EXAMPLE 4a

Preparation of cocrystalline 2-(2,6-dichlorophenyl)-1-(1S,3R)-5-(2-hydroxy-2-methylpropyl)-3-(hydroxymethyl)-1-methyl-3,4-dihydroisoquinolin-2(1H)-yl)ethan-1-one and 4-hydroxybenzoic acid Place 2-(2,6-dichlorophenyl)-1-((1S,3R)-5-(2-hydroxy-2-methylpropyl)-3-(hydroxymethyl)-1-methyl-3,4-dihydroisoquinolin-2(1H)-yl)ethan-1-one (98.33 mg) and of 4-hydroxybenzoic acid (35.40 mg) in a 20 mL vial equipped with a stir bar. The vial is filled to the brim with water (~20 mL) and slurried at 45° C. (stirplate setting) overnight. The sample is slurried further over the 48 hours at 60° C. with no crystals formed. Acetone (1 mL) is added, and the sample is slurried overnight at 40° C./1000 rpm. The material appears crystalline. The resulting white solid is isolated by vacuum filtration and dried in place under vacuum and air stream for 10 minutes.

X-Ray Powder Diffraction

The X-ray diffraction (XRD) patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of 0.2 in 2θ will take into account these potential variations without hindering the unequivocal identification of the indicated crystal form. Confirmation of a crystal form may be made based on any unique combination of distinguishing peaks (in units of °2θ), typically the more prominent peaks. (United States Pharmacopeia #35, National Formulary #30, Chapter <941>, pages 427-432, 2012). The crystal form diffraction patterns, collected at ambient temperature and relative humidity, are adjusted based on NBS standard reference material 675 (mica) with peaks at 8.85 and 26.77 degrees 2-theta.

A prepared sample of Example 4a co-crystal is characterized by an X-ray diffraction pattern using CuKa radiation as having diffraction peaks (2-theta values) as described in Table 11 below, and in particular having peaks at 7.0 in combination with one or more of the peaks selected from the group consisting of 18.8, 16.1, and 19.3; with a tolerance for the diffraction angles of 0.2 degrees.

TABLE 11

X-ray powder diffraction peaks of Example 4a

| Peak | Angle (°2-Theta) | Intensity (%) |
|---|---|---|
| 1 | 7.0 | 100.0 |
| 2 | 13.6 | 52.5 |
| 3 | 15.1 | 68.4 |
| 4 | 16.1 | 91.9 |
| 5 | 18.8 | 96.0 |
| 6 | 19.3 | 81.0 |
| 7 | 19.9 | 65.3 |
| 8 | 21.6 | 68.8 |
| 9 | 24.5 | 76.4 |
| 10 | 25.5 | 48.9 |

EXAMPLE 7

Synthesis of 2-(2-chloro-6-methoxy-phenyl)-1-[(1S,3R)-3-(hydroxymethyl)-5-(3-hydroxy-3-methyl-butyl)-1-methyl-3,4-dihydro-1H-isoquinolin-2-yl]ethanone

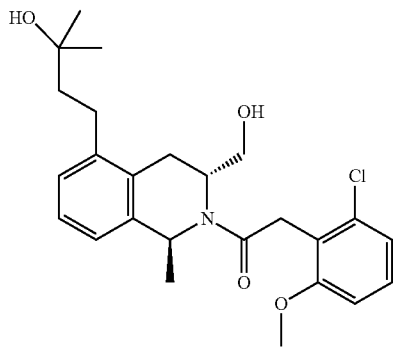 [SMILES: COc1cccc(Cl)c1CC(=O)N1[C@@H](CO)Cc2c(CCC(C)(C)O)cccc2[C@@H]1C]

Dissolve 1-[(1S,3R)-3-[[tert-butyl(dimethyl)silyl]oxymethyl]-5-(3-hydroxy-3-methyl-butyl)-1-methyl-3,4-dihydro-1H-isoquinolin-2-yl]-2-(2-chloro-6-methoxy-phenyl)ethanone (0.58 g, 1.04 mmol) in THF (5.3 mL). Add acetic acid (16 mL, 279 mmol) and water (5.3 mL). Stir at 50° C. for 1.5 hours. Concentrate under reduced pressure. Dissolve the residue in ethyl acetate and wash with saturated sodium bicarbonate solution, water, and brine. Dry over sodium sulfate, filter, and concentrate under reduced pressure. Purify the residue by silica gel chromatography, eluting with acetone:hexanes (gradient, 0-30%) to give the title compound as a white foam (0.34 g, 0.76 mmol). MS (m/z): 446.0 (M+1).

The following compound is prepared essentially by the method of Example 8.

| Example No. | Name | Structure | Physical Data |
|---|---|---|---|
| 8 | 2-(2-chloro-5-methoxy-phenyl)-1-[(1S,3R)-3-(hydroxymethyl)-5-(3-hydroxy-3-methyl-butyl)-1-methyl-3,4-dihydro-1H-isoquinolin-2-yl]ethanone | 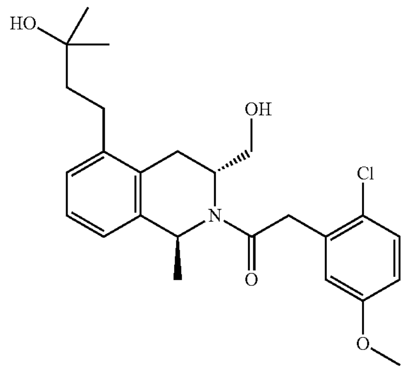 [SMILES: COc1ccc(Cl)c(CC(=O)N2[C@@H](CO)Cc3c(CCC(C)(C)O)cccc3[C@@H]2C)c1] | MS (m/z): 446.0 (M + 1). |
| 9 | 2-(6-chloro-2-fluoro-3-methoxy-phenyl)-1-[(1S,3R)-3-(hydroxymethyl)-5-(3-hydroxy-3-methyl-butyl)-1-methyl-3,4-dihydro-1H-isoquinolin-2-yl]ethanone | 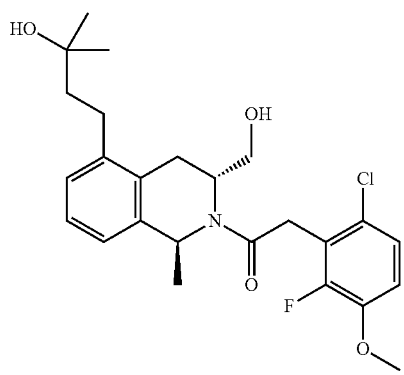 [SMILES: COc1ccc(Cl)c(CC(=O)N2[C@@H](CO)Cc3c(CCC(C)(C)O)cccc3[C@@H]2C)c1F] | MS (m/z): 463.8 (M + 1). |

EXAMPLE 10

Synthesis of 2-(2-chlorophenyl)-1-[(1S,3R)-3-(hydroxymethyl)-5-(3-hydroxy-3-methyl-butyl)-1-methyl-3,4-dihydro-1H-isoquinolin-2-yl]ethanone

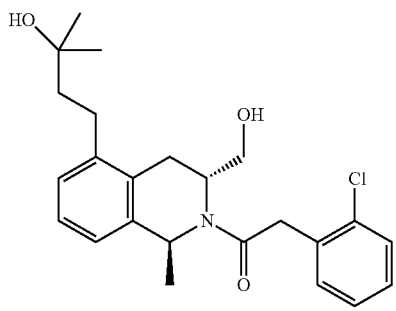 [SMILES: C[C@H]1c2cccc(CCC(C)(C)O)c2C[C@H](CO)N1C(=O)Cc1ccccc1Cl]

Dissolve 2-(2-chlorophenyl)acetic acid (96.8 mg, 0.56 mmol) and O-(7-aza-1H-benzotriazol-1-yl)-N,N,N',N'-tetramethyluronium hexafluorophosphate (200 mg, 0.52 mmol) in dichloromethane (2 mL). Add diisopropylethylamine (183 µL, 1.05 mmol). Stir at ambient temperature for 20 min. Add this reaction mixture to a solution of 4-[(1S,3R)-3-(hydroxymethyl)-1-methyl-1,2,3,4-tetrahydroisoquinolin-5-yl]-2-methyl-butan-2-ol (92 mg, 0.35 mol) in dichloromethane (0.4 mL). Rinse with dichloromethane (1 mL) and stir at ambient temperature for 3.5 hours. Dilute the reaction mixture with water and stir. Extract with dichloromethane and dry the extracts over sodium sulfate, filter, and concentrate under reduced pressure. Purify the residue by silica gel chromatography, eluting with ethyl acetate: hexanes (gradient, 0-60%) to give a residue. Purify the residue by silica gel chromatography, eluting with 10% (2N ammonia in methanol): dichloromethane to give the title compound as a white foam (78 mg, 0.19 mmol). MS (m/z): 416.2 (M+1).

The following compound is prepared essentially by the method of Example 10.

| Example No. | Name | Structure | Physical Data |
|---|---|---|---|
| 11 | 2-(2-chloro-6-fluoro-phenyl)-1-[(1S,3R)-3-(hydroxymethyl)-5-(3-hydroxy-3-methyl-butyl)-1-methyl-3,4-dihydro-1H-isoquinolin-2-yl]ethanone | 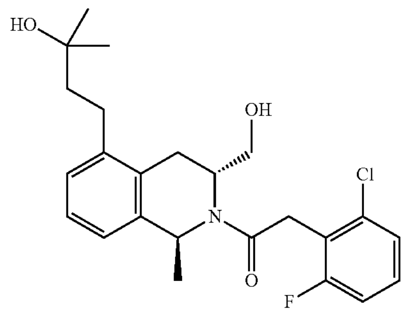 [SMILES: C[C@H]1c2cccc(CCC(C)(C)O)c2C[C@H](CO)N1C(=O)Cc1c(F)cccc1Cl] | MS (m/z): 434.2 (M + 1). |

EXAMPLE 12

Synthesis of 3-chloro-2-[2-[(1S,3R)-3-(hydroxymethyl)-5-(3-hydroxy-3-methyl-butyl)-1-methyl-3,4-dihydro-1H-isoquinolin-2-yl]-2-oxo-ethyl]benzonitrile

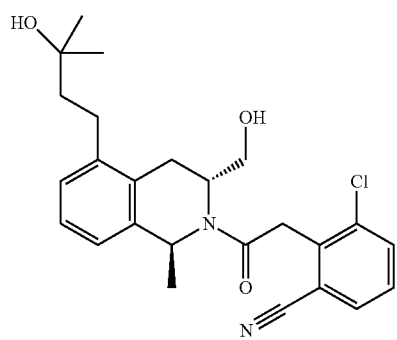 [SMILES: C[C@H]1c2cccc(CCC(C)(C)O)c2C[C@H](CO)N1C(=O)Cc1c(Cl)cccc1C#N]

In a vial slurry 2-(2-chloro-6-cyano-phenyl)acetic acid (75.4 mg, 0.37 mmol) in acetonitrile (0.3 mL). Add triethylamine (114 µL, 0.82 mmol) and stir until the solids dissolve. Add O-(benzotriazol-1-yl)-N,N,N',N'-tetramethyluronium tetrafluoroborate (165 mg, 0.51 mmol) and stir at ambient temperature for 10 min. In a separate flask slurry 4-[(1S,3R)-3-(hydroxymethyl)-1-methyl-1,2,3,4-tetrahydroisoquinolin-5-yl]-2-methyl-butan-2-ol hydrochloride (102 mg, 0.34 mol) in acetonitrile (0.3 mL). Add triethylamine (227 µL, 1.63 mmol) and a precipitate forms. Stir 10 min at ambient temperature. Transfer the 2-(2-chloro-6-cyano-phenyl)acetic acid, acetonitrile, triethylamine, and O-(benzotriazol-1-yl)-N,N,N',N'-tetramethyluronium tetrafluoroborate reaction mixture from the vial to the flask containing the 4-[(1S,3R)-3-(hydroxymethyl)-1-methyl-1,2,3,4-tetrahydroisoquinolin-5-yl]-2-methyl-butan-2-ol hydrochloride, acetonitrile and triethylamine reaction mixture. Rinse with acetonitrile (0.9 mL) and stir the homogeneous reaction mixture at ambient temperature overnight. Dilute the reaction mixture with water and extract with ethyl acetate. Wash the ethyl acetate extracts with water, saturated sodium bicarbonate solution and brine. Dry the extracts over sodium sulfate, filter, and concentrate under reduced pressure. Purify the residue by silica gel chromatography, eluting with ethyl acetate: hexanes (0-60% gradient) to give a residue. Purify by reverse phase chromatography on C18 modified silica to yield the title compound as a green oil (34 mg, 0.08 mmol): (m/z): 441.2 (M+1).

Preparation 46

Synthesis of 2-(2-chloro-6-methyl-phenyl)acetic acid

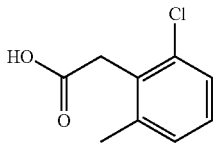

To a 100 mL screw-cap vial add 2-(2-chloro-6-methyl-phenyl)acetonitrile (8.0 g, 48.30 mmol) and 3N aqueous sodium hydroxide (80 mL, 240.00 mmol). Heat the mixture at 110° C. for 18 hr. Cool the mixture to 10° C. and acidify to pH 1 with concentrated hydrochloric acid (15 mL). Extract the mixture with ethyl acetate. Separate and dry the organic phase over sodium sulfate. Filter, and concentrate to dryness. Crystallize from diethyl ether to yield the title compound as an off white solid (7.20 g, 39.00 mmol): MS (m/z): 184.8 (M+1).

Preparation 47

Synthesis of tert-butyl 2-(2-chloro-5-isopropyl-phenyl)acetate

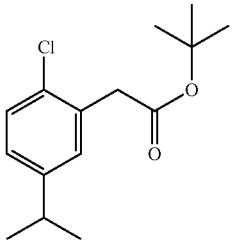 [SMILES: CC(C)c1ccc(Cl)c(CC(=O)OC(C)(C)C)c1]

Add bis(dibenzylideneacetone)palladium (49.2 mg, 85.6 µmol) to a round bottom flask and seal with a septum. Flush with nitrogen. Add tri-tert-butylphosphine (85.6 µL, 85.6 µmol, 1M in toluene) and lithium bis(trimethylsilyl)amide (12.8 mL, 11.56 mmol, 0.9M in methylcyclohexanes) via a syringe. Add 2-bromo-1-chloro-4-isopropyl-benzene (1.0 g, 4.28 mmol) and t-butyl acetate (865.2 μL, 6.42 mmol) via a syringe. Add toluene (10.7 mL) via a syringe and the reaction mixture becomes hot to the touch. Place on an ambient temperature water bath and stir for 3 hours. Store the reaction mixture in the freezer over the weekend. Warm the reaction mixture to ambient temperature. Dilute the reaction mixture with diethyl ether and add saturated ammonium chloride solution. Separate the layers and wash the diethyl ether layer with saturated sodium chloride solution. Dry over sodium sulfate, filter and concentrate under reduced pressure. Purify the residue by silica gel chromatography eluting with acetone: hexanes (0-2% gradient) to give the title compound (1.04 g). Purify again by silica gel chromatography eluting with dichloromethane: hexanes (0-20% gradient) to give the title compound (490 mg, 1.82 mmol). MS (m/z): 213.0 (M-tBu+1).

The following compound is prepared essentially by the method of Preparation 47.

| Prep. No. | Name | Structure | Physical data |
|---|---|---|---|
| 48 | tert-butyl 2-(2-chloro-5-ethyl-phenyl)acetate | 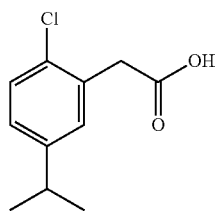 | MS (m/z): 198.8 (M − tBu + 1). |

Preparation 49

Synthesis of 2-(2-chloro-5-isopropyl-phenyl)acetic acid

Dissolve tert-butyl 2-(2-chloro-5-isopropyl-phenyl)acetate (483 mg, 1.80 mmol) in dichloromethane (5.1 mL). Add trifluoroacetic acid (1.09 mL, 14.4 mmol) slowly and stir the reaction mixture 3 hours at ambient temperature. Concentrate under reduced pressure to give the title compound (380 mg, 1.79 mmol). MS (m/z): 229.8 (M+18). The following compound is prepared essentially by the method of Preparation 49.

| Prep. No. | Name | Structure | Physical data |
|---|---|---|---|
| 50 | 2-(2-chloro-5-ethyl-phenyl)acetic acid | 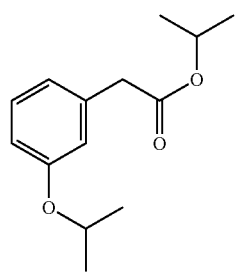 | MS (m/z): 215.8 (M + 18) |

Preparation 51

Synthesis of isopropyl 2-(3-isopropoxyphenyl)acetate

Dissolve 2-(3-hydroxyphenyl)acetic acid (5.04 g, 32.8 mmol) in dimethylformamide (49.9 mL). Add potassium carbonate (15.1 g, 108.2 mmol) and 2-iodopropane (15.1 mL, 150.8 mmol). Heat the reaction mixture to 80° C. for 6 hours. Stir at ambient temperature for 64 hours. Heat the reaction mixture to 95° C. for 6 hours.

Add additional potassium carbonate (9.2 g, 65.6 mmol) and 2-iodopropane (15.1 mL, 150.8 mmol) and heat the reaction mixture to 90° C. overnight. Raise the temperature of the reaction mixture to 150° C. and heat overnight. Cool to ambient temperature and concentrate under reduced pressure. Dilute the residue with water and ethyl acetate. Separate the layers and extract the water layer with ethyl acetate. Combine the ethyl acetate extracts and wash with water and brine, dry over sodium sulfate, filter and concentrate under reduced pressure. Purify the residue by silica gel chromatography eluting with acetone: hexanes (0-20% gradient) to give the title compound (4.79 g, 20.27 mmol). MS (m/z): 237.0 (M+H), 254.0 (M+18).

The following compound is prepared essentially by the method of Preparation 51.

| Prep. No. | Name | Structure | Physical data |
|---|---|---|---|
| 52 | Ethyl 2-(2-chloro-5-ethoxy-phenyl)acetate | 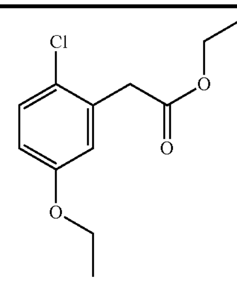 | MS (m/z): 243.0 (M + 1) 260.0 (M + 18). |

Preparation 53

Synthesis of 2-(3-isopropoxyphenyl)acetic acid

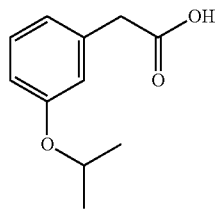

Dissolve isopropyl 2-(3-isopropoxyphenyl)acetate (4.2 g, 17.8 mmol) in tetrahydrofuran (35.6 mL). Add water (35.6 mL) and lithium hydroxide (6.05 g, 248.8 mmol). Heat the reaction mixture to 66° C. overnight. Concentrate under reduced pressure to remove the tetrahydrofuran. Dilute the reaction mixture with water and wash with diethyl ether. Acidify the water layer with 5N HCl to pH 1. Extract the water layer with diethyl ether. Wash the diethyl ether extract with water and brine, dry over sodium sulfate, filter and concentrate under reduced pressure to give the title compound (3.37 g, 17.35 mmol). MS (m/z): 195.0 (M+1), 212.0 (M+18).

The following compound is prepared essentially by the method of Preparation 53.

| Prep. No. | Chemical name | Structure | Physical data |
|---|---|---|---|
| 54 | 2-(2-chloro-5-ethoxy-phenyl)acetic acid | 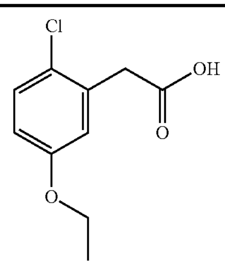 | MS (m/z): 232.0 (M + 18). |

Preparation 55

Synthesis of 2-(2-chloro-5-isopropoxy-phenyl)acetic acid

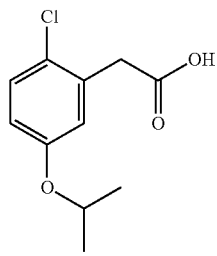

Dissolve 2-(3-isopropoxyphenyl)acetic acid (3.24 g, 16.6 mmol) in dimethylformamide (11.1 mL). Cool on an ice bath and add a solution N-chlorosuccinimide (2.44 g, 18.3 mmol) in dimethylformamide (12.2 mL). Stir overnight allowing the reaction to reach ambient temperature. Dilute the reaction mixture with diethyl ether. Wash with water. Extract the water wash with diethyl ether. Combine the diethyl ether extracts and wash with water and brine, dry over sodium sulfate, filter and concentrate under reduced pressure. Purify the residue by silica gel chromatography eluting with acetone: hexanes (0-25% gradient) to give the title compound (3.08 g, 13.47 mmol). MS (m/z): 245.8 (M+18).

The following compound is prepared essentially by the method of Preparation 55.

| Prep. No. | Name | Structure | Physical data |
|---|---|---|---|
| 56 | 2-(2-chloro-5-hydroxy-phenyl)acetic acid | 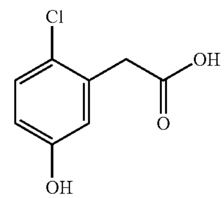 [SMILES: O=C(O)Cc1cc(O)ccc1Cl] | MS (m/z): 203.8 (M + 18). |

Preparation 57

Synthesis of methyl 2-(2-chloro-6-cyano-phenyl)acetic acid

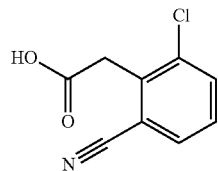 [SMILES: N#Cc1cccc(Cl)c1CC(=O)O]

Add a 2M solution of lithium diisopropylamide in tetrahydrofuran (62.6 mL, 461.8 mmol) to tetrahydrofuran (1 L) at −78° C. Slowly add 1,3-dimethyl-3,4,5,6-tetrahydro-2(1H)-pyrimidinone (19.94 mL, 164.91 mmol) followed by dropwise addition of 3-chloro-2-methyl-benzonitrile (20 g, 131.93 mmol). Maintain the mixture at −78° C. with stirring for 5 min. Purge the reaction vessel with carbon dioxide (1 L; 25.65 moles) for 15 min. Add water (100 mL) and stir for 2 hr. Add 10M aqueous solution of sodium hydroxide to increase the pH of the aqueous phase to >12. Separate the aqueous layer and wash with diethyl ether. Acidify the aqueous layer with concentrated hydrochloric acid to pH-1 and extract with ethyl acetate. Separate the organic phase and dry over sodium sulfate. Filter and concentrate to dryness to yield the title compound as an off white solid (16.0 g; 81.80 mmol). MS (m/z): 195.9 (M+1).

Preparation 58

Synthesis of methyl (1S,3R)-3-[[tert-butyl(dimethyl)silyl]oxymethyl]-1-methyl-1,2,3,4-tetrahydroisoquinoline-5-carboxylate

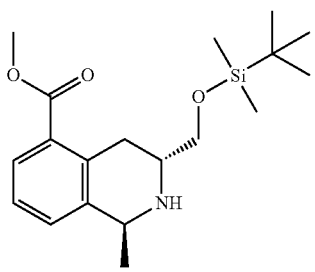 [SMILES: COC(=O)c1cccc2c1C[C@H](CO[Si](C)(C)C(C)(C)C)N[C@H]2C]

In a glass pressure vessel, containing a magnetic stirrer bar, suspend (1S,3R)-5-bromo-3-((tert-butyldimethylsilyloxy)methyl)-1-methyl-1,2,3,4-tetrahydroisoquinoline (30 g, 81.0 mmol), palladium acetate (1.8 g, 8.1 mmol), bis-(1,3-diphenylphosphino)propane (6.7 g, 16.2 mmol) and sodium carbonate (34.3 g, 324.0 mmol) in a mixture of dimethyl sulfoxide (360 mL) and methanol (180 mL). Charge the vessel with carbon monoxide (410 kPa) and warm to 100° C. with stirring. Maintain temperature at 100° C. for 19 hours. Allow the mixture to cool to ambient temperature. Filter the resulting suspension and dilute the filtrate with methyl tert-butyl ether (1000 mL). Wash the solution with brine (3×500 mL). Dry over sodium sulfate, filter and concentrate under reduced pressure to yield the title compound as a dark orange oil (26.7 g, 76.4 mmol): MS (m/z): 350.0 (M+1).

Preparation 59

Synthesis of methyl (1S,3R)-3-[[tert-butyl(dimethyl)silyl]oxymethyl]-2-[2-(6-chloro-2-fluoro-3-methoxy-phenyl)acetyl]-1-methyl-3,4-dihydro-1H-isoquinoline-5-carboxylate

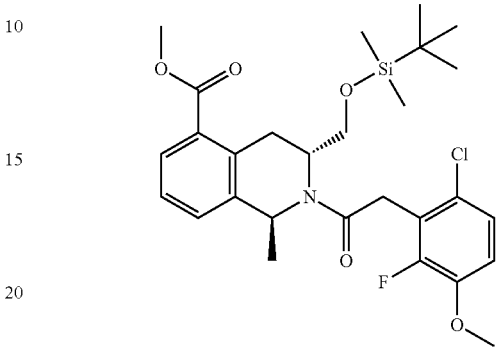

Add triethylamine (0.36 mL, 2.57 mmol) to a stirred solution of methyl (1S,3R)-3-[[tert-butyl(dimethyl)silyl]oxymethyl]-1-methyl-1,2,3,4-tetrahydroisoquinoline-5-carboxylate (500 mg, 1.29 mmol), (benzotriazol-1-yloxy)tripyrrolidinophosphonium hexafluorophosphate (1.02 g, 1.93 mmol) and 2-(6-chloro-2-fluoro-3-methoxy-phenyl)acetic acid (356 mg, 1.54 mmol) in dimethylformamide (6.4 mL). Stir at room temperature for 16 h. Add saturated aqueous ammonium chloride (60 mL). Extract with ethyl acetate (3×50 mL). Wash the combined organic layers with brine. Dry over magnesium sulfate, filter and concentrate under reduced pressure. Purify by flash chromatography to yield the title compound as an amorphous yellow solid (703 mg, 1.15 mmol): MS (m/z): 550.0 (M+1).

The following compounds are prepared essentially by the method of Preparation 59.

| Prep. No. | Name | Structure | Physical data |
|---|---|---|---|
| 60 | methyl (1S,3R)-3-[[tert-butyl(dimethyl)silyl]oxymethyl]-2-[2-(2-chloro-6-fluoro-3-methyl-phenyl)acetyl]-1-methyl-3,4-dihydro-1H-isoquinoline-5-carboxylate | 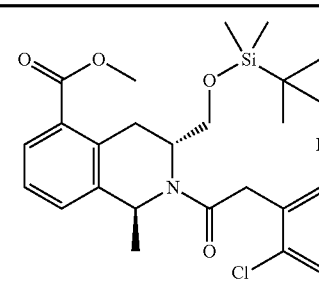 | MS (m/z): 534.0 (M + 1). |
| 61 | methyl (1S,3R)-3-[[tert-butyl(dimethyl)silyl]oxymethyl]-2-[2-(2-chloro-6-methyl-phenyl)acetyl]-1-methyl-3,4-dihydro-1H-isoquinoline-5-carboxylate | 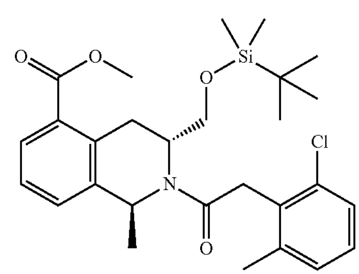 [SMILES: COC(=O)c1cccc2c1C[C@H](CO[Si](C)(C)C(C)(C)C)N(C(=O)Cc1c(C)cccc1Cl)[C@H]2C] | MS (m/z): 516.0 (M + 1). |

| Prep. No. | Name | Structure | Physical data |
|---|---|---|---|
| 62 | methyl (1S,3R)-3-[[tert-butyl(dimethyl)silyl]oxymethyl]-2-[2-(2-chloro-5-methyl-phenyl)acetyl]-1-methyl-3,4-dihydro-1H-isoquinoline-5-carboxylate | 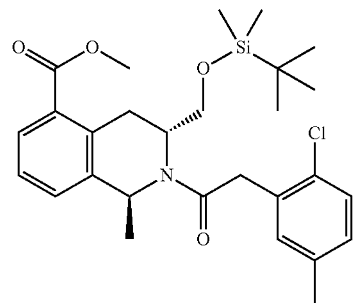 [SMILES: COC(=O)c1cccc2c1C[C@H](CO[Si](C)(C)C(C)(C)C)N(C(=O)Cc1cc(C)ccc1Cl)[C@H]2C] | MS (m/z): 516.0 (M + 1). |
| 63 | methyl (1S,3R)-3-[[tert-butyl(dimethyl)silyl]oxymethyl]-2-[2-(2-chloro-6-fluoro-phenyl)acetyl]-1-methyl-3,4-dihydro-1H-isoquinoline-5-carboxylate | 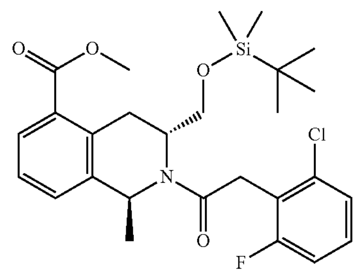 [SMILES: COC(=O)c1cccc2c1C[C@H](CO[Si](C)(C)C(C)(C)C)N(C(=O)Cc1c(F)cccc1Cl)[C@H]2C] | MS (m/z): 520.2 (M + 1). |
| 64 | methyl (1S,3R)-3-[[tert-butyl(dimethyl)silyl]oxymethyl]-2-[2-(2-chloro-5-methoxy-phenyl)acetyl]-1-methyl-3,4-dihydro-1H-isoquinoline-5-carboxylate | 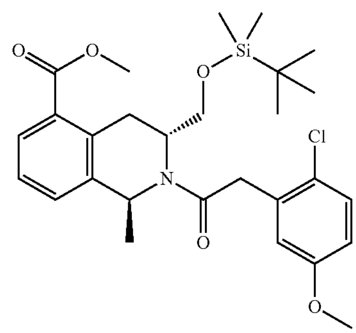 [SMILES: COC(=O)c1cccc2c1C[C@H](CO[Si](C)(C)C(C)(C)C)N(C(=O)Cc1cc(OC)ccc1Cl)[C@H]2C] | MS (m/z): 532.2 (M + 1). |
| 65 | methyl (1S,3R)-3-[[tert-butyl(dimethyl)silyl]oxymethyl]-2-[2-(2-chloro-6-methoxy-phenyl)acetyl]-1-methyl-3,4-dihydro-1H-isoquinoline-5-carboxylate | 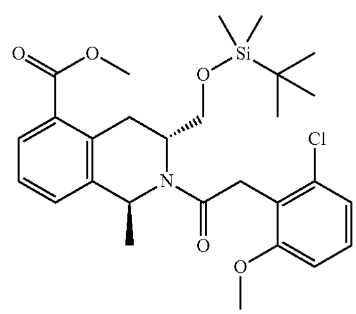 [SMILES: COC(=O)c1cccc2c1C[C@H](CO[Si](C)(C)C(C)(C)C)N(C(=O)Cc1c(Cl)cccc1OC)[C@H]2C] | MS (m/z): 532.1 (M + 1). |
| 66 | methyl (1S,3R)-3-[[tert-butyl(dimethyl)silyl]oxymethyl]-2-[2-(2-chloro-5-isopropyl-phenyl)acetyl]-1-methyl-3,4-dihydro-1H-isoquinoline-5-carboxylate | 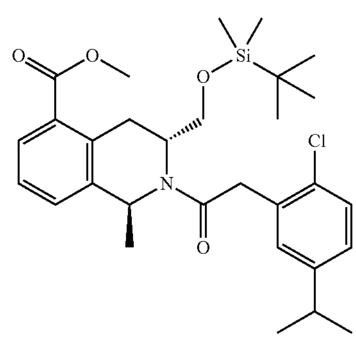 [SMILES: COC(=O)c1cccc2c1C[C@H](CO[Si](C)(C)C(C)(C)C)N(C(=O)Cc1cc(C(C)C)ccc1Cl)[C@H]2C] | MS (m/z): 544.0 (M + 1). |

-continued

| Prep. No. | Name | Structure | Physical data |
|---|---|---|---|
| 67 | methyl (1S,3R)-3-[[tert-butyl(dimethyl)silyl]oxymethyl]-2-[2-(2-chloro-5-ethoxy-phenyl)acetyl]-1-methyl-3,4-dihydro-1H-isoquinoline-5-carboxylate | 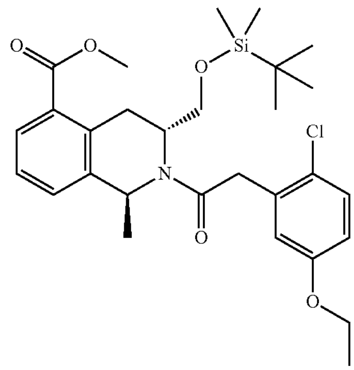 [SMILES: CCOc1ccc(Cl)c(CC(=O)N2[C@@H](CO[Si](C)(C)C(C)(C)C)Cc3c(C(=O)OC)cccc3[C@@H]2C)c1] | MS (m/z): 545.8 (M + 1) |
| 68 | methyl (1S,3R)-3-[[tert-butyl(dimethyl)silyl]oxymethyl]-2-[2-(2-chloro-5-ethyl-phenyl)acetyl]-1-methyl-3,4-dihydro-1H-isoquinoline-5-carboxylate | 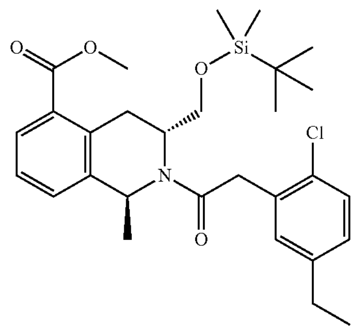 [SMILES: CCc1ccc(Cl)c(CC(=O)N2[C@@H](CO[Si](C)(C)C(C)(C)C)Cc3c(C(=O)OC)cccc3[C@@H]2C)c1] | MS (m/z): 529.9 (M + 1) |
| 69 | methyl (1S,3R)-3-[[tert-butyl(dimethyl)silyl]oxymethyl]-2-[2-(2-chloro-6-cyano-phenyl)acetyl]-1-methyl-3,4-dihydro-1H-isoquinoline-5-carboxylate | 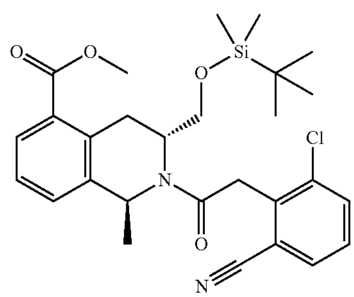 [SMILES: COC(=O)c1cccc2c1C[C@H](CO[Si](C)(C)C(C)(C)C)N(C(=O)Cc1c(Cl)cccc1C#N)[C@H]2C] | MS (m/z): 527.0 (M + 1). |
| 70 | methyl (1S,3R)-3-[[tert-butyl(dimethyl)silyl]oxymethyl]-2-[2-(6-chloro-2-fluoro-3-methyl-phenyl)acetyl]-1-methyl-3,4-dihydro-1H-isoquinoline-5-carboxylate | 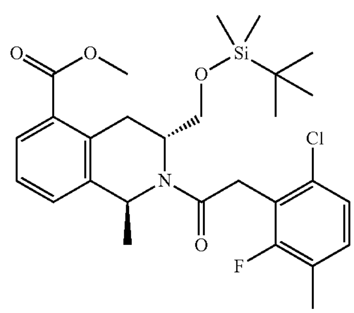 [SMILES: COC(=O)c1cccc2c1C[C@H](CO[Si](C)(C)C(C)(C)C)N(C(=O)Cc1c(Cl)ccc(C)c1F)[C@H]2C] | MS (m/z): 534.0 (M + 1). |
| 71 | methyl (1S,3R)-3-[[tert-butyl(dimethyl)silyl]oxymethyl]-2-[2-(2-chlorophenyl)acetyl]-1-methyl-3,4-dihydro-1H-isoquinoline-5-carboxylate | 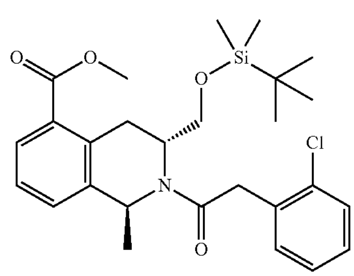 [SMILES: COC(=O)c1cccc2c1C[C@H](CO[Si](C)(C)C(C)(C)C)N(C(=O)Cc1ccccc1Cl)[C@H]2C] | MS (m/z): 502.0 (M + 1). |

| Prep. No. | Name | Structure | Physical data |
|---|---|---|---|
| 72 | methyl (1S,3R)-2-[2-(2-bromophenyl)acetyl]-3-[[tert-butyl(dimethyl)silyl]oxymethyl]-1-methyl-3,4-dihydro-1H-isoquinoline-5-carboxylate | 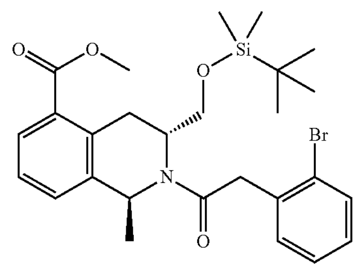 [SMILES: COC(=O)c1cccc2c1C[C@H](CO[Si](C)(C)C(C)(C)C)N(C(=O)Cc1ccccc1Br)[C@H]2C] | MS (m/z): 545.8, 547.8 (M + 1) |
| 73 | methyl (1S,3R)-3-[[tert-butyl(dimethyl)silyl]oxymethyl]-2-[2-(2-chloro-5-fluorophenyl)acetyl]-1-methyl-3,4-dihydro-1H-isoquinoline-5-carboxylate | 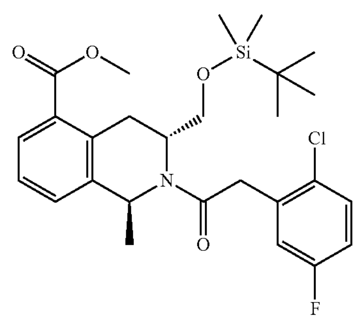 [SMILES: COC(=O)c1cccc2c1C[C@H](CO[Si](C)(C)C(C)(C)C)N(C(=O)Cc1cc(F)ccc1Cl)[C@H]2C] | MS (m/z): 520.0 (M + 1). |
| 74 | methyl (1S,3R)-3-[[tert-butyl(dimethyl)silyl]oxymethyl]-2-[2-(2,5-dichlorophenyl)acetyl]-1-methyl-3,4-dihydro-1H-isoquinoline-5-carboxylate | 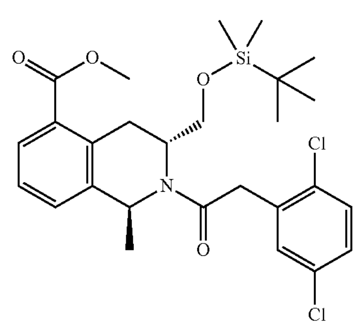 [SMILES: COC(=O)c1cccc2c1C[C@H](CO[Si](C)(C)C(C)(C)C)N(C(=O)Cc1cc(Cl)ccc1Cl)[C@H]2C] | MS (m/z): 536.0 (M + 1). |
| 75 | methyl (1S,3R)-3-[[tert-butyl(dimethyl)silyl]oxymethyl]-2-[2-(2-chloro-5-isopropoxyphenyl)acetyl]-1-methyl-3,4-dihydro-1H-isoquinoline-5-carboxylate | 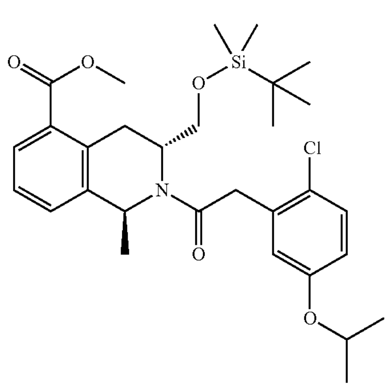 [SMILES: COC(=O)c1cccc2c1C[C@H](CO[Si](C)(C)C(C)(C)C)N(C(=O)Cc1cc(OC(C)C)ccc1Cl)[C@H]2C] | MS (m/z): 560.2 (M + 1). |

| Prep. No. | Name | Structure | Physical data |
|---|---|---|---|
| 76 | methyl (1S,3R)-3-[[tert-butyl(dimethyl)silyl]oxymethyl]-2-[2-(2,6-difluoro-3-methyl-phenyl)acetyl]-1-methyl-3,4-dihydro-1H-isoquinoline-5-carboxylate | 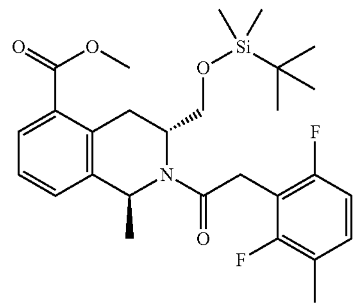 | MS (m/z): 518.0 (M + 1). |
| 77 | methyl (1S,3R)-3-[[tert-butyl(dimethyl)silyl]oxymethyl]-2-[2-(2,6-difluorophenyl)acetyl]-1-methyl-3,4-dihydro-1H-isoquinoline-5-carboxylate | 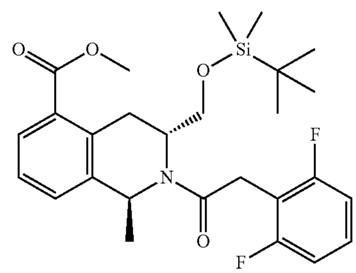 [SMILES: COC(=O)c1cccc2c1C[C@H](CO[Si](C)(C)C(C)(C)C)N(C(=O)Cc1c(F)cccc1F)[C@H]2C] | MS (m/z): 504.0 (M + 1). |
| 78 | methyl (1S,3R)-3-[[tert-butyl(dimethyl)silyl]oxymethyl]-2-[2-(2-chloro-6-fluoro-3-methoxy-phenyl)acetyl]-1-methyl-3,4-dihydro-1H-isoquinoline-5-carboxylate | 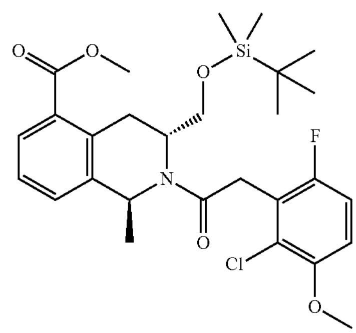 [SMILES: COC(=O)c1cccc2c1C[C@H](CO[Si](C)(C)C(C)(C)C)N(C(=O)Cc1c(F)ccc(OC)c1Cl)[C@H]2C] | MS (m/z): 550.0 (M + 1). |

EXAMPLE 13

Synthesis of 2-(6-chloro-2-fluoro-3-methoxy-phenyl)-1-[(1S,3R)-3-(hydroxymethyl)-5-(1-hydroxy-1-methyl-ethyl)-1-methyl-3,4-dihydro-1H-isoquinolin-2-yl]ethanone

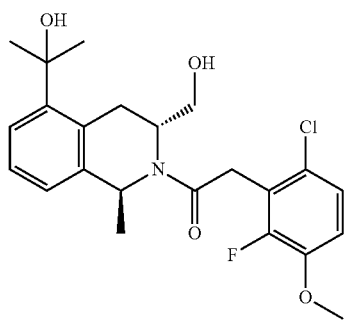 [SMILES: COc1ccc(Cl)c(CC(=O)N2[C@@H](CO)Cc3c(cccc3C(C)(C)O)[C@@H]2C)c1F]

Add 0.6M solution of lanthanum (III) chloride bis(lithium chloride) complex in tetrahydrofuran (1.92 mL, 1.15 mmol) to a stirred solution of methyl (1S,3R)-3-[[tert-butyl(dimethyl)silyl]oxymethyl]-2-[2-(6-chloro-2-fluoro-3-methoxy-phenyl)acetyl]-1-methyl-3,4-dihydro-1H-isoquinoline-5-carboxylate (703 mg, 1.15 mmol) in tetrahydrofuran (5 mL). Stir at room temperature for 40 minutes. Add 3M solution of methyl magnesium bromide in diethyl ether (3.50 equiv; 4.03 mmol; 1.34 mL; 1.39 g) dropwise. Stir the reaction mixture for 1.5 h. Quench with brine (25 mL). After gas evolution has ceased, extract with ethyl acetate (3×25 mL). Wash the combined organic layers with brine. Dry over magnesium sulfate, filter and concentrate under reduced pressure. Redissolve residue in tetrahydrofuran (10 mL) and add tetrabutylammonium fluoride, trihydrate (492 mg, 1.73 mmoles). Stir for 2 h at room temperature. Concentrate under reduced pressure. Wash the residue through a short flash silica pad (15 g) with ethyl acetate (50 mL). Concentrate under reduced pressure. Purify by reverse phase chromatography on C18 modified silica to yield the title compound as a white solid (349 mg, 0.76 mmol): (m/z): 436.0 (M+1).

The following compounds are prepared essentially by the method of Example 13.

| Example No. | Name | Structure | Physical Data |
|---|---|---|---|
| 14 | 2-(2-chloro-6-fluoro-3-methyl-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 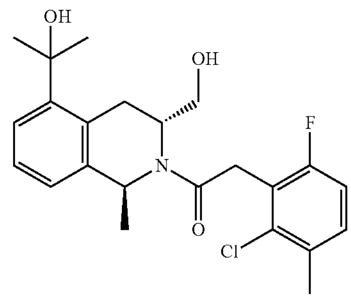 [SMILES: Cc1ccc(F)c(CC(=O)N2[C@@H](CO)Cc3c(cccc3C(C)(C)O)[C@@H]2C)c1Cl] | MS (m/z): 420.2 (M + 1). |
| 15 | 2-(2-chloro-6-methyl-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 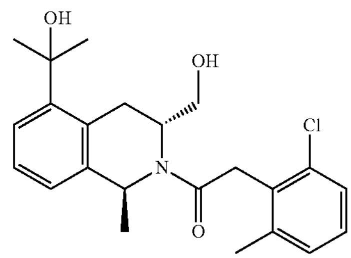 [SMILES: Cc1cccc(Cl)c1CC(=O)N1[C@@H](CO)Cc2c(cccc2C(C)(C)O)[C@@H]1C] | MS (m/z): 402.0 (M + 1). |
| 16 | 2-(2-chloro-5-methyl-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 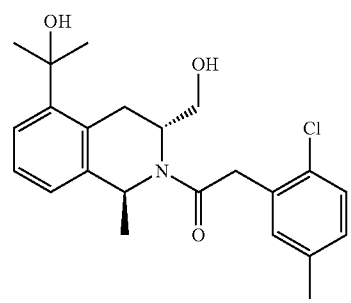 [SMILES: Cc1ccc(Cl)c(CC(=O)N2[C@@H](CO)Cc3c(cccc3C(C)(C)O)[C@@H]2C)c1] | MS (m/z): 402.0 (M + 1). |
| 17 | 2-(2-chloro-6-fluoro-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 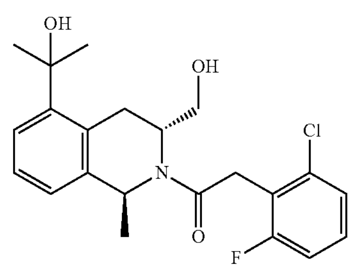 [SMILES: C[C@H]1c2cccc(C(C)(C)O)c2C[C@H](CO)N1C(=O)Cc1c(F)cccc1Cl] | MS (m/z): 406.0 (M + 1). |
| 18 | 2-(2-chloro-5-methoxy-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 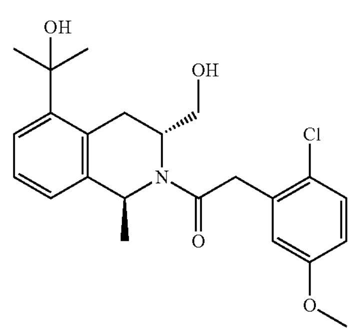 [SMILES: COc1ccc(Cl)c(CC(=O)N2[C@@H](CO)Cc3c(cccc3C(C)(C)O)[C@@H]2C)c1] | MS (m/z): 418.0 (M + 1). |

-continued

| Example No. | Name | Structure | Physical Data |
|---|---|---|---|
| 19 | 2-(2-chloro-6-methoxy-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 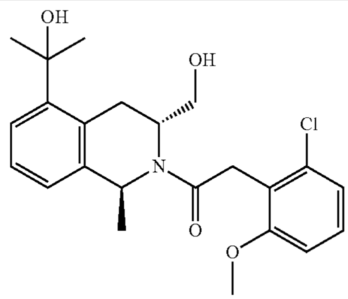 [SMILES: COc1cccc(Cl)c1CC(=O)N1[C@@H](CO)Cc2c(cccc2C(C)(C)O)[C@@H]1C] | MS (m/z): 418.0 (M + 1). |
| 20 | 2-(2-chloro-5-isopropyl-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 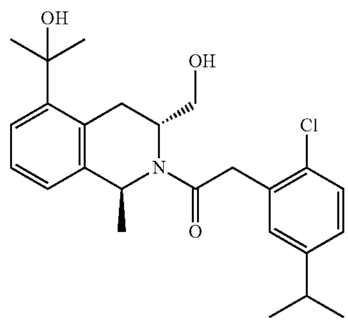 [SMILES: CC(C)c1ccc(Cl)c(CC(=O)N2[C@@H](CO)Cc3c(cccc3C(C)(C)O)[C@@H]2C)c1] | MS (m/z): 430.0 (M + 1). |
| 21 | 2-(2-chloro-5-ethoxy-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 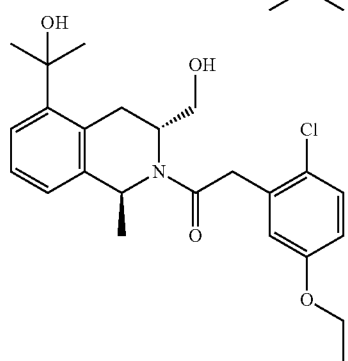 | MS (m/z): 432.2 (M + 1). |
| 22 | 2-(2-chloro-5-ethyl-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 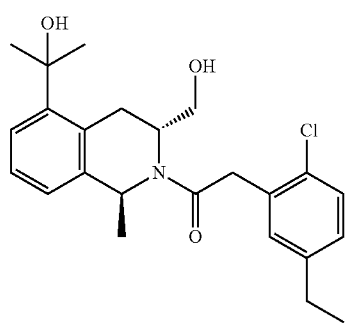 [SMILES: CCc1ccc(Cl)c(CC(=O)N2[C@@H](CO)Cc3c(cccc3C(C)(C)O)[C@@H]2C)c1] | MS (m/z): 416.0 (M + 1). |
| 23 | 3-chloro-2-[2-[(1S,3R)-3-(hydroxymethyl)-5-(1-hydroxy-1-methyl-ethyl)-1-methyl-3,4-dihydro-1H-isoquinolin-2-yl]-2-oxo-ethyl]benzonitrile | 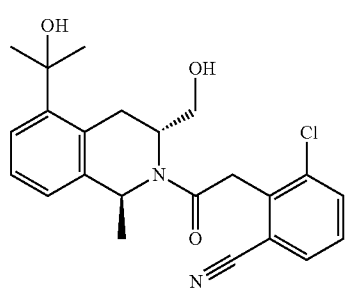 [SMILES: C[C@H]1c2cccc(C(C)(C)O)c2C[C@H](CO)N1C(=O)Cc1c(Cl)cccc1C#N] | MS (m/z): 413.0 (M + 1). |

-continued

| Example No. | Name | Structure | Physical Data |
|---|---|---|---|
| 24 | 2-(6-chloro-2-fluoro-3-methyl-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 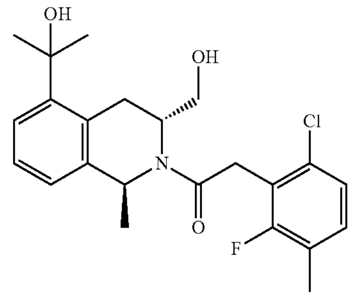 [SMILES: Cc1ccc(Cl)c(CC(=O)N2[C@@H](CO)Cc3c(cccc3C(C)(C)O)[C@@H]2C)c1F] | MS (m/z): 420.0 (M + 1). |
| 25 | 2-(2-chlorophenyl)-1-[(1S,3R)-3-(hydroxymethyl)-5-(1-hydroxy-1-methyl-ethyl)-1-methyl-3,4-dihydro-1H-isoquinolin-2-yl]ethanone | 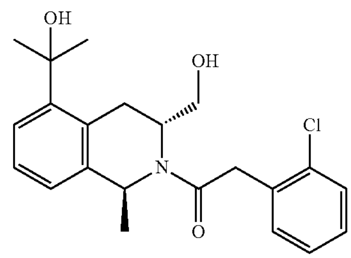 [SMILES: C[C@H]1c2cccc(C(C)(C)O)c2C[C@H](CO)N1C(=O)Cc1ccccc1Cl] | MS (m/z): 388.0 (M + 1). |
| 26 | 2-(2-bromophenyl)-1-[(1S,3R)-3-(hydroxymethyl)-5-(1-hydroxy-1-methyl-ethyl)-1-methyl-3,4-dihydro-1H-isoquinolin-2-yl]ethanone | 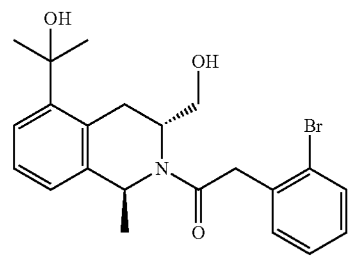 | MS (m/z): 431.8, 433.8 (M + 1). |
| 27 | 2-(2-chloro-5-fluoro-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 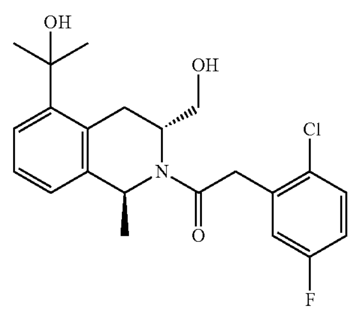 [SMILES: C[C@H]1c2cccc(C(C)(C)O)c2C[C@H](CO)N1C(=O)Cc1cc(F)ccc1Cl] | MS (m/z): 406.0 (M + 1). |
| 28 | 2-(2,5-dichlorophenyl)-1-[(1S,3R)-3-(hydroxymethyl)-5-(1-hydroxy-1-methyl-ethyl)-1-methyl-3,4-dihydro-1H-isoquinolin-2-yl]ethanone | 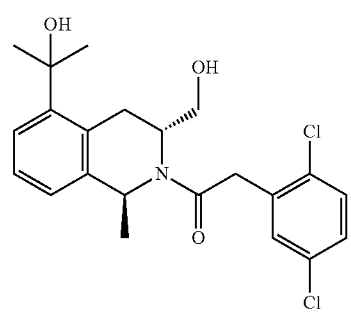 [SMILES: C[C@H]1c2cccc(C(C)(C)O)c2C[C@H](CO)N1C(=O)Cc1cc(Cl)ccc1Cl] | MS (m/z): 422.0 (M + 1). |

| Example No. | Name | Structure | Physical Data |
|---|---|---|---|
| 29 | 2-(2-chloro-5-isopropoxy-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 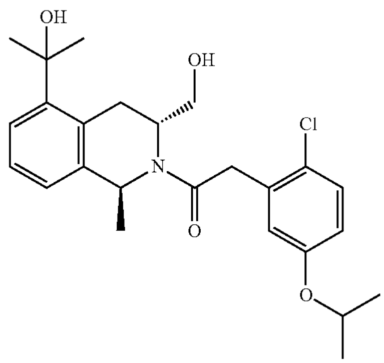 [SMILES: CC(C)Oc1ccc(Cl)c(CC(=O)N2[C@@H](CO)Cc3c(cccc3C(C)(C)O)[C@@H]2C)c1] | MS (m/z): 445.8 (M + 1). |
| 30 | 2-(2,6-difluoro-3-methyl-phenyl)-1-[(1S,3R)-3-(hydroxymethyl)-5-(1-hydroxy-1-methyl-ethyl)-1-methyl-3,4-dihydro-1H-isoquinolin-2-yl]ethanone | 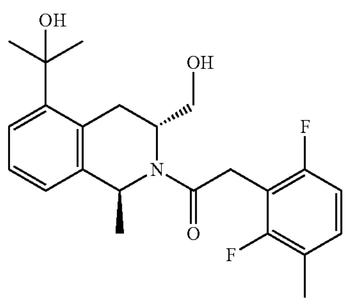 [SMILES: Cc1ccc(F)c(CC(=O)N2[C@@H](CO)Cc3c(cccc3C(C)(C)O)[C@@H]2C)c1F] | MS (m/z): 404.0 (M + 1). |
| 31 | 2-(2,6-difluorophenyl)-1-[(1S,3R)-3-(hydroxymethyl)-5-(1-hydroxy-1-methyl-ethyl)-1-methyl-3,4-dihydro-1H-isoquinolin-2-yl]ethanone | 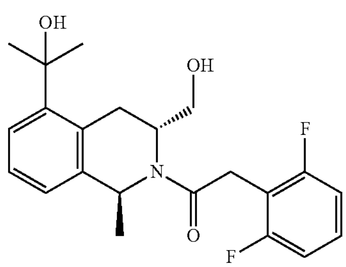 [SMILES: C[C@H]1c2cccc(C(C)(C)O)c2C[C@H](CO)N1C(=O)Cc1c(F)cccc1F] | MS (m/z): 390.2 (M + 1). |
| 32 | 2-(2-chloro-6-fluoro-3-methoxy-phenyl)-1-[(1S,3R)-3-(hydroxymethyl)-5-(1-hydroxyl-1-methyl-ethyl)-1-methyl-3,4-dihydro-1H-isoquinolin-2-yl]ethanone | 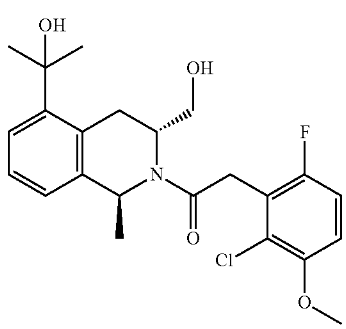 | MS (m/z): 436.2 (M + 1). |

We claim:
1. A compound of the formula

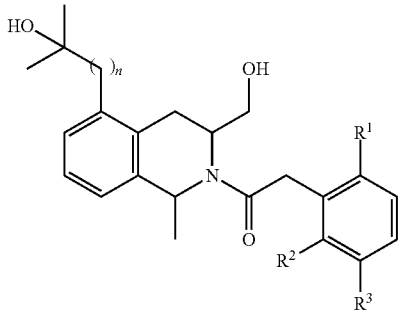

wherein
n is 0, 1 or 2;
$R^1$ is halogen;
$R^2$ is halogen, H, CN, C1-C3 alkoxy or C1-C3 alkyl; and
$R^3$ is H, halogen, C1-C3 alkoxy or C1-C3 alkyl.

2. The compound according to claim 1 of the formula

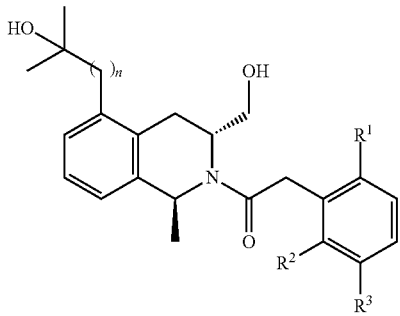

wherein
n is 0, 1 or 2;
$R^1$ is halogen;
$R^2$ is halogen, H, CN, C1-C3 alkoxy or C1-C3 alkyl; and
$R^3$ is H, halogen, C1-C3 alkoxy or C1-C3 alkyl.

3. The compound according to either claim 1 or 2 wherein
n is 0, 1 or 2;
$R^1$ is halogen;
$R^2$ is halogen; and
$R^3$ is hydrogen or C1-C3 alkoxy.

4. The compound according to either claim 1 or 2 wherein
n is 0, 1 or 2;
$R^1$ is Cl, F or Br;
$R^2$ is Cl, $OCH_3$, H, F, CN or $CH_3$; and
$R^3$ is $OCH_3$, H, $CH_2CH_3$, Cl, $OCH(CH_3)_2$, $OCH_2CH_3$, F, $CH(CH_3)_2$ or $CH_3$.

5. The compound according to either claim 1 or 2 wherein
n is 0 or 2;
$R^1$ is Cl;
$R^2$ is Cl or F; and
$R^3$ is H or $OCH_3$.

6. The compound according to claim 1 which is 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone.

7. A composition comprising 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid.

8. A cocrystalline form of the composition according to claim 7.

9. The cocrystalline form of the composition according to claim 8 characterized by an X-ray powder diffraction pattern using CuKα radiation having a diffraction peak at diffraction angle 2-theta of 18.2° in combination with one or more of the peaks selected from the group consisting of 16.0°, 25.4°, and 7.0°; with a tolerance for the diffraction angles of 0.2 degrees.

10. A pharmaceutical composition comprising 2-(2,6-dichlorophenyl)-1-[(1S,3R)-3-(hydroxymethyl)-5-(3-hydroxy-3-methylbutyl)-1-methyl-3,4-dihydroisoquinolin-2(1H)-yl]ethanone and 4-hydroxybenzoic acid, and a pharmaceutically acceptable carrier, diluent or excipient.

11. A pharmaceutical composition comprising a compound according to claim 1, and a pharmaceutically acceptable carrier, diluent or excipient.

12. A method of treating Parkinson's disease comprising administrating to a patient in need thereof an effective amount of a compound according to claim 1.

13. A method of treating schizophrenia comprising administrating to a patient in need thereof an effective amount of a compound according to claim 1.

* * * * *